(12) United States Patent
Murray

(10) Patent No.: US 9,233,140 B2
(45) Date of Patent: Jan. 12, 2016

(54) TREATMENT METHODS FOR HYPERSENSITIVE DISORDERS

(75) Inventor: Lynne Anne Murray, King of Prussia, PA (US)

(73) Assignee: Promedior, Inc., Lexington, MA (US)

( * ) Notice: Subject to any disclaimer, the term of this patent is extended or adjusted under 35 U.S.C. 154(b) by 1040 days.

(21) Appl. No.: 12/720,847

(22) Filed: Mar. 10, 2010

(65) Prior Publication Data

US 2010/0266578 A1 Oct. 21, 2010

Related U.S. Application Data

(60) Provisional application No. 61/209,795, filed on Mar. 11, 2009.

(51) Int. Cl.
*A61K 38/17* (2006.01)

(52) U.S. Cl.
CPC .................................. *A61K 38/1716* (2013.01)

(58) Field of Classification Search
None
See application file for complete search history.

(56) References Cited

U.S. PATENT DOCUMENTS

| | | | |
|---|---|---|---|
| 4,233,969 A | 11/1980 | Lock et al. |
| 4,556,056 A | 12/1985 | Fischer et al. |
| 4,782,014 A | 11/1988 | Serban et al. |
| 5,092,876 A | 3/1992 | Dhawan et al. |
| 5,272,258 A | 12/1993 | Siegel et al. |
| 5,591,709 A | 1/1997 | Lindenbaum |
| 5,654,186 A | 8/1997 | Cerami et al. |
| 5,698,589 A | 12/1997 | Allen |
| 5,750,345 A | 5/1998 | Bowie |
| 5,804,446 A | 9/1998 | Cerami et al. |
| 5,846,796 A | 12/1998 | Cerami et al. |
| 5,989,811 A | 11/1999 | Veltri et al. |
| 6,037,458 A | 3/2000 | Hirai et al. |
| 6,054,121 A | 4/2000 | Cerami et al. |
| 6,071,517 A | 6/2000 | Fanger et al. |
| 6,126,918 A | 10/2000 | Pepys et al. |
| 6,174,526 B1 | 1/2001 | Cerami et al. |
| 6,365,570 B1 | 4/2002 | Van Kessel et al. |
| 6,406,698 B1 | 6/2002 | Svehang et al. |
| 6,537,811 B1 | 3/2003 | Freier |
| 6,600,019 B2 | 7/2003 | Prayaga et al. |
| 6,660,843 B1 | 12/2003 | Feige et al. |
| 6,872,541 B2 | 3/2005 | Mills |
| 7,666,432 B2 | 2/2010 | Gomer et al. |
| 7,763,256 B2 | 7/2010 | Gomer et al. |
| 8,012,472 B2 | 9/2011 | Gomer et al. |
| 8,057,802 B2 | 11/2011 | Gomer et al. |
| 8,187,599 B2 | 5/2012 | Gomer et al. |
| 8,187,608 B2 | 5/2012 | Gomer et al. |
| 8,247,370 B2 | 8/2012 | Pelura |
| 8,329,659 B2 | 12/2012 | Willett |
| 8,497,243 B2 | 7/2013 | Hesson et al. |
| 2002/0058284 A1 | 5/2002 | Winkel |
| 2003/0003567 A1 | 1/2003 | Barber et al. |
| 2003/0022245 A1 | 1/2003 | Mills |
| 2003/0162180 A1 | 8/2003 | Pricop |
| 2004/0068095 A1 | 4/2004 | Shimkets et al. |
| 2004/0121343 A1 | 6/2004 | Buechler et al. |
| 2005/0182042 A1 | 8/2005 | Feldman et al. |
| 2005/0238620 A1 | 10/2005 | Gomer et al. |
| 2007/0048855 A1 | 3/2007 | Gamez et al. |
| 2007/0065368 A1 | 3/2007 | Gomer et al. |
| 2007/0065866 A1 | 3/2007 | Gomer et al. |
| 2008/0038192 A1 | 2/2008 | Gervais |
| 2008/0044429 A1 | 2/2008 | Johnson et al. |
| 2009/0074754 A1 | 3/2009 | Hesson et al. |
| 2009/0074771 A1 | 3/2009 | Koenig et al. |
| 2009/0202520 A1 | 8/2009 | Lupher, Jr. et al. |
| 2010/0111898 A1 | 5/2010 | Pelura |
| 2010/0260781 A1 | 10/2010 | Murray |
| 2010/0266578 A1 | 10/2010 | Murray |
| 2010/0317596 A1 | 12/2010 | Willett et al. |
| 2010/0323970 A1 | 12/2010 | Willett |

FOREIGN PATENT DOCUMENTS

| | | |
|---|---|---|
| EP | 0 206 302 A2 | 12/1986 |
| EP | 1090630 A1 | 4/2001 |
| JP | 11-319542 | 11/1999 |
| WO | WO 92/21364 A1 | 12/1992 |
| WO | WO 94/27640 A1 | 12/1994 |
| WO | WO 95/05394 A1 | 2/1995 |
| WO | WO 95/33454 A1 | 12/1995 |
| WO | WO 97/16568 A1 | 5/1997 |
| WO | WO 97/26906 A1 | 7/1997 |

(Continued)

OTHER PUBLICATIONS

Rudinger, in "Peptide Hormones" (ed. J.A. Parsons), university Park Press, Baltimore, pp. 1-7 (1975).*
Hogaboam et al, "Chronic Airway Hyperreactvity, Goblet Cell Hyperplasia, and Peribronchial Fibrosis during Allergic Airway Disease Induced by Aspergillus fumigatus," American Journal of Phatology, vol. 156(2), pp. 723-732, XP55041065 (2000).
Moreira et al., "Serum amyloid P attenuates M2 macrophage activation and protects against fungal spore-induced allergic airway disease," Journal of Allergy and Clinical Immunology, vol. 126(4), pp. 712-721, XP027422131 (2010).
Tennent et al., "Macrophage dependent elimination of amyloid following treatment with ant-iSAP antibody," Amyloid: The International Journal of Experimental and Clinical Investigation, vol. 17(1); p. 51, XP009163874 (2010).
Abe, R., et al., "Peripheral Blood Fibrocytes: Differentiation Pathway and Migration to Wound Sites," The Journal of Immunology, 166(12):7556-7562 (2001).
Agostini, et al., "Chemokine/Cytokine Cocktail in Idiopathic Pulmonary Fibrosis," Proc. Am. Thorac. Soc., 3:357-363 (2006).

(Continued)

*Primary Examiner* — Robert C Hayes
(74) *Attorney, Agent, or Firm* — Ropes & Gray LLP

(57) ABSTRACT

The current standard of care for the treatment of allergic airway diseases include short and long acting beta-agonists, and inhaled or systemic corticosteroids, cromolyn and xanthines that all have the potential of detrimental side-effects. The present invention describes a new mechanistic protein-based therapeutic approach for the treatment of allergic airway disease and diseases associated with excessive Th2 pathology. The present invention relates to the surprising discovery that serum amyloid P (SAP) demonstrates a therapeutic affect in the treatment of hypersensitive disorders.

6 Claims, 9 Drawing Sheets

(56) References Cited

FOREIGN PATENT DOCUMENTS

| | | |
|---|---|---|
| WO | WO 99/41285 A1 | 8/1999 |
| WO | WO 99/45900 A1 | 9/1999 |
| WO | WO 01/74300 A1 | 10/2001 |
| WO | WO 03/031572 A2 | 4/2003 |
| WO | WO 03/097104 A1 | 11/2003 |
| WO | WO 2004/009823 A1 | 1/2004 |
| WO | WO 2004/016750 A2 | 2/2004 |
| WO | WO 2004/058292 A2 | 7/2004 |
| WO | WO 2004/059293 A2 | 7/2004 |
| WO | WO 2004/059318 A2 | 7/2004 |
| WO | WO 2004/076486 A1 | 9/2004 |
| WO | WO 2005/110474 A2 | 11/2005 |
| WO | WO 2005/115452 A2 | 12/2005 |
| WO | WO 2006/002438 A2 | 1/2006 |
| WO | WO 2006/002930 A2 | 1/2006 |
| WO | WO 2006/028956 A2 | 3/2006 |
| WO | WO 2006/039418 A2 | 4/2006 |
| WO | WO 2007/047207 A2 | 4/2007 |
| WO | WO 2007/047796 A2 | 4/2007 |
| WO | WO 2008/070117 A1 | 6/2008 |
| WO | WO 2009/009019 A2 | 1/2009 |
| WO | WO 2009/009034 A2 | 1/2009 |
| WO | WO 2010/104959 A1 | 9/2010 |
| WO | WO 2010/104961 A1 | 9/2010 |
| WO | WO 2010/115032 A1 | 10/2010 |
| WO | WO 2010/141918 A1 | 12/2010 |

OTHER PUBLICATIONS

Aiba, S., et al., "Immunoglobulin-Producing Cells in Plasma Cell Orificial Mucositis," Journal of Cutaneous Pathology, 16:207-210 (1989).

Alles, V. V., et al., "Inducible expression of PTX3, a new member of the pentraxin family, in human mononuclear phagocytes," Blood, 84(10):3483-3493 (1994).

Ashcroft, T., et al., "Simple Method of Estimating Severity of Pulmonary Fibrosis on a Numerical Scale," J Clin Pathol, 41(4):467-470 (1988).

Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169:6490-6497 (2002).

Azuma, H., et al., "Superagonistic CD28 Antibody Induces Donor-Specific Tolerance in Rat Renal Allografts," American Journal of Transplantation, 8:2004-2014 (2008).

Bain, J., et al., "The Specificities of Protein Kinase Inhibitors: An Update," Biochem. J, 371(Pt 1):199-204 (2003).

Barna, B. P., et al., "Activation of Human Monocyte Tumoricidal Activity by C-Reactive Protein," Cancer Research, 47:3959-3963 (1987).

Bharadwaj et al., "Serum Amyloid P Component Binds to Fc gamma Receptors and Opsonizes Particles for Phagocytosis," The Journal of Immunology, 166:6735-6741 (2001).

Bharadwaj, D., et al., "The Major Receptor for C-Reactive Protein on Leukocytes Is Fcγ Receptor II," The Journal of Experimental Medicine, 190(4):585-590 (1999).

Bickerstaff, M. C. M., et al., "Serum Amyloid P Component Controls Chromatin Degradation and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Booth, D. R., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," The Journal of Immunology, 166(7):4498-4506 (2001).

Castaño, A. P., et al., "Serum Amyloid P Inhibits Fibrosis Through FcγR-Dependent Monocyte-Macrophage Regulation in Vivo," Sci. Transl. Med. 1(5):1-26 (2009).

Chatziantoniou, et al., "Is Kidney Injury a Reversible Process," Curr. Opin. Nephrol. Hypertension, 17(1):76-81 (2008).

Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).

Chesney, J., et al., "Peripheral Blood Fibrocytes: Mesenchymal Precursor Cells and the Pathogenesis of Fibrosis," Curr. Rheumatology Reports, 2(6):501-505 (2000).

Chesney, J., et al., "Regulated Production of Type I Collagen and Inflammatory Cytokines by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRIIa on HL-60 Granulocytes," The Journal of Immunology, 168:1413-1418 (2002).

Christner, R. B., et al., "Binding of Human Serum Amyloid P-Component to Phosphocholine", Archives of Biochemistry and Biophysics, 314(2):337-343 (1994).

Clark, R. A. F., "Fibrin and Wound Healing," Annals New York Academy of Sciences 936:355-367 (2001).

Crouch, E., "Pathobiology of Pulmonary Fibrosis," Am J Physiol Lung Cell Mol Physiol, 259(4 Pt 1):L159-L184 (1990).

D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).

Daëron, M., "Fc Receptor Biology," Annual Review of Immunology 15:203-234 (1997).

Daëron, M., "Structural Bases of FcγR Functions," Int Rev Immunol. 16(1-2):1-27 (1997).

De Beer, F. C., et al., "Fibronectin and C4-Binding Protein are Selectively Bound by Aggregated Amyloid Component", J Exp Med., 154(4):1134-1149 (1981).

De Beer, F. C., et al., "Isolation and Characterization of C-Reactive Protein and Serum Amyloid P Component in the Rat," Immunology 45(1):55-70 (1982).

De Beer, F. C., et al., "Isolation of Human C-Reactive Protein and serum Amyloid P Component," Journal of Immunological Methods, 50(1):17-31 (1982).

de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).

De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.

Du Clos, T. W., "C-Reactive Protein Reacts With the U1 Small Nuclear Ribonucleoprotein," The Journal of Immunology, 143(8):2553-2559 (1989).

(56) References Cited

OTHER PUBLICATIONS

Du Clos, T. W., et al., "Reply to Human C-reactive protein does not bind to FcγRIIa on phagocytic cells," The Journal of Clinical Investigation, vol. 107(5):643 (2001).
Duchemin, A. M., et al., "Association of Non-Receptor Protein Tyrosine Kinases with the FcγRI/γ-Chain Complex in Monocytic Cells," The Journal of Immunology, 158(2):865-871 (1997).
Duckworth, et al., "The Structure of Agar Part I. Fractionation of a Complex Mixture of Polysaccharides," Carbohydrate Research, 16:189-197 (1971).
Emsley, J., et al., "Structure of Pentameric Human Serum Amyloid P Component," Nature 367(6461):338-345 (1994).
Flesch, B. K., et al., "The FCGR2A—Arg131 Variant is no Major Mortality Factor in the Elderly—Evidence From a German Centenarian Study," International Journal of Immunogenetics, 33(4):277-279 (2006).
Garden, A. S., et al., "Head and Neck Radiation and Mucositis," 1(1):30-34 (2007).
Gehring, et al., "Effect of Topically Applied Dexpanthenol on Epidermal Barrier Function and Stratum Corneum Hydration," Arzneim-Forsch./Drug Res., 50(11):7 (2000).
Gerhard, et al., "The Status, Quality and Expansion of the NIH Full-Length cDNA Project: The Mammalian Gene Collection (MGC)," Genome Research, 14(10B):2121-2127 (2004).
Gewurz, H., et al., "Structure and Function of the Pentraxins," Current Opinion in Immunology, 7(1):54-64 (1995).
Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).
Giorgini, A., et al., "Blockade of Chronic Graft-Versus-Host Disease by Alloantigen-induced CD4+CD25+Foxp3+ Regulatory T Cells in Nonlymphopenic Hosts," Journal of Leukocyte Biology, 82(5):1053-1061 (2007).
Giri, S., et al., "Antifibrotic Effect of Decorin in a Bleomycin Hamster Model of Lung Fibrosis," Biochemical Pharmacology, 54:1205-1216 (1997).
Gregory, S. G., et al., "The DNA Sequence and Biological Annotation of Human Chromosome 1", Nature 441(7091):315-321 (2006).
Guyre, C. A., et al., "Receptor Modulation by FcγRI-Specific Fusion Proteins is Dependent on Receptor Number and Modified by IgG," The Journal of Immunology, 167(11):6303-6311 (2001).
Hamazaki, Hideaki, "Structure and significance of N-linked sugar unit of human serum amyloid P component," Biochimica et Biochimica Acta, 1037(3):435-438 (1990).
Harris, J. M., et al., "Pegylation A Novel Process for Modifying Pharmacokinetics," Clin. Pharmacokinetics, 40(7):539-551 (2001).
Hartlapp, I., et al., "Fibrocytes Induce an Angiogenic Phenotype in Cultured Endothelial Cells and Promote Angiogenesis in Vivo," The FASEB Journal, 15(12):2215-2224 (2001).
Heegaard, N. H. H., et al., "Ligand-Binding Sites in Human Serum Amyloid P Component," Eur. J. Biochem. 239(3):850-856 (1996).
Hicks et al., "Serum amyloid P component binds to histones and activates the classical complement pathway", The Journal of Immunology, 149:3689-3694 (1992).
Hind, C. R. K., et al., "Human Serum Amyloid P Component, a Circulating Lectin with Specificity for the Cyclic 4,6-Pyruvate Acetal of Galactose: Interactions with Various Bacteria", Biochem.J., 225(1):107-111 (1985).
Hind, C. R., et al, "Binding specificity of serum amyloid P-component for the pyruvate acetal of galactose," Journal of Experimental Medicine, 159(4):1058-1069 (1984).
Hohenester, E., et al., "Crystal Structure of a Decameric Complex of Human Serum Amyloid P Component with Bound dAMP", J. Mol. Biol. 269(4):570-578 (1997).
Huang, Z. Y., et al., "The Monocyte Fcγ Receptors FcγRI/γ and FcγRIIA Differ in their Interaction with Syk and with Src-Related Tyrosine Kinases," J Leukoc Biol 76(2):491-499 (2004).
Hutchinson, W. L., et al., "Human Serum Amyloid P Component is a Single Uncomplexed Pentamer in Whole Serum," Molecular Medicine, 6(6):482-493 (2000).

International Search Report, PCT/US2010/026838, dated May 17, 2010.
Ishaque, et al., "Role of Vitamins in Determining Apoptosis and Extent of Suppression by bcl-2 During hybridoma Cell Culture," Apoptosis, 7(3):231-239 (2002).
Janeway, et al., Immunobiology, 3rd edition, Garland Publishing, pp. 3:1-3:11 (1997).
Jenny, N.S., et al., "Serum Amyloid P and Cardiovascular Disease in Older Men and Women Results from the Cardiovascular Health Study," Arterioscler. Thromb. Vasc. Biol., 27:352-358 (2007).
Junqueira, L. C.,et al., "Picrosirius Straining Plus Polarization Microscopy, a Specific Method for Collagen Detection in Tissue Sections," Histochem. J, 11(4):447-455 (1979).
Kessel, A., et al., Intravenous Immunoglobulin Therapy Affects T Regulatory Cells by Increasing Their Suppressive Function, The Journal of Immunology, 179(8):5571-5575 (2007).
Kiernan et al., "Proteomic Characterization of Novel Serum Amyloid P Component Variants from Human Plasm and Urine," Proteomics, 4:1825-1829 (2004).
Kiernan, U.A., et al., "Selected Expression Profiling of Full-Length Proteins and Their Variants from Human Plasma," Clin. Proteomics 1:7-16 (2004).
Kinoshita CM, et al., "A Protease-Sensitive Site in the Proposed Ca2+-Binding Region of Human Serum Amyloid Component and Other Pentraxins." Protein Sci., 1:700-709 (1992).
Kisseleva, T., et al., "Bone Marrow-Derived Fibrocytes Participate in Pathogenesis of Liver Fibrosis," Journal of Hepatology, 45(3):429-438 (2006).
Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2000).
Kolstoe et al., "Molecular Dissection of Alzheimer's Disease Neuropathology by Depletion of Serum Amyloid P Component", PNAS, 106(18):7619-7623 (2009).
Korade-Mirnics, Z., et al., "Src Kinase-Mediated Signaling in Leukocytes," J Leukoc Biol., 68(5):603-613 (2003).
Kucuk, H. F., et al., "Effect of a Selective Cyclooxygenase-2 Inhibitor on Renal Scarring," European Surgical Research, 38(5):451-457 (2006).
Lai, J. Y., et al., "Potent Small Molecule Inhibitors of Spleen Tyrosine Kinase (Syk)," Bioorganic & Medicinal Chemistry Letters, 13(18):3111-3114 (2003).
Lei, K. K., et al., "Genomic DNA Sequence for Human C-Reactive Protein," J. Biol. Chem. 260(24):13377-13383 (1985).
Lindenbaum, E. S., et al., "Serum-Free Cell Culture Medium Induces Acceleration of Wound Healing in Guinea-Pigs," Burns, 21(2):110-115 (1995).
Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).
Lu, J., et al., "Structural Recognition and Functional Activation of FcγR by Innate Pentraxins," Nature, 456(7224):989-992 (2008).
Majno, G., "Chronic Inflammation: Links With Angiogenesis and Wound Healing," American Journal of Pathology, 153(4):1035-1039 (1998).
Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).
Marnell, L. L., et al., "C-Reactive Protein Binds to FcγRI in Transfected COS Cells," The Journal of Immunology, 155(4):2185-193 (1995).
Metz, C. N., "Fibrocytes: A Unique Cell Population Implicated in Wound Healing," Cell. Mol. Life Sci., 60(7):1342-1350 (2003).
Mold, C., et al., "Serum Amyloid P Component and C-Reactive Protein Mediate Phagocytosis Through Murine FcγRs," The Journal of Immunology, 166(2):1200-1205 (2001).
Moore, B. B., et al., "CCR2-Mediated Recruitment of Fibrocytes to the Alveolar Space After Fibrotic Injury," American Journal of Pathology, 166(3):675-684 (2005).
Mori, L., et al., "Fibrocytes Contribute to the Myofibroblast Population in Wounded Skin and Originate From the Bone Marrow," Exp Cell Res., 304(1):81-90 (2005).

(56) References Cited

OTHER PUBLICATIONS

Mortensen, R. F., et al., "Regulation of phagocytic leukocyte activities by C-reactive protein," Journal of Leukocyte Biology, 67(4):495-500 (2000).

Murphy, T. M., et al., "Extrahepatic Transcription of Human C-Reactive Protein," Journal of Experimental Medicine, 73(2):495-498 (1991).

Murray et al., "Serum Amyloid P Therapeutically Attenuates Murine Bleomycin-Induced Pulmonary Fibrosis Via its Effects on Macrophages," PloS One, 5(3):e968 pp. 1-9 (2010).

Ohnishi, S. et al., "Isolation and Characterization of the Complete Complementary and Genomic DNA Sequences of Human Serum Amyloid P Component," J. Biochem, 100(4):849-858 (1986).

Oliveira, E. B., et al., "Primary Structure of Human C-Reactive Protein," The Journal of Biological Chemistry, 254(2):489-502 (1979).

Oriente, A., et al., "Interleukin-13 Modulates Collagen Homeostasis in Human Skin and Keloid Fibroblasts," The Journal of Pharmacology and Experimental Therapeutics, 292(3):988-994 (2000).

Osmand, A. P., et al., Partial Amino-Acid Sequences of Human and Rabbit C-Reactive Proteins: Homology with Immunoglobulins and Histocompatibility Antigens, Proc. Natl. Acad. Sci. U.S.A., 74(3):1214-1218 (1977).

Pachence, J., et al., "Tissue-Activated Delivery—Novel Methods for Site-Directed Drug Delivery," Drug Delivery Technology, 3(1):40-45 (2003).

Painter, R. H., "Evidence that C1t (Amyloid P-component) is not a subcomponent of the first component of complement (C1)," J. Immunol., 119(6):2203-2205 (1977).

Paul, William E., M.D., Editor, Fundamental Immunology, 3d Ed. Raven Press, p. 242 (1993).

Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998).

Pepys et al., Glycobiology of Human Serum Amyloid P Component Amyloid Amyloidosis, *Proc. Int. Symp. Amyloidosis*, pp. 177-179 (1994).

Pepys, et al., "Targeted Pharmacological Depletion of Serum Amyloid P Component for Treatment of Human Amyloidosis", *Nature*, 471:254-259 (2002).

Pepys, et al., Human Serum Amyloid P Component is an Invariant Constituent of Amyloid Deposits and has a Uniquely Homogeneous Glycostructure, PNAS, 91:5206-5606 (1994).

Pepys, M. B., "Isolation of Serum Amyloid P-Component (Protein SAP) in the Mouse," Immunology, 37(3):637-641 (1979).

Pepys, M. B., et al., "Amyloid P Component. A Critical Review," Amyloid: Int. J. Exp. Invest., 4(4):274-295 (1997).

Philips, R. J., et al., "Circulating Fibrocytes Traffic to the Lungs in Response to CXCL 12 and Mediate Fibrosis," The Journal of Clinical Investigation, 114(3):438-446 (2004).

Pilling et al., "Aggregated IgG inhibits the differentiation of human fibrocytes," *Journal of Leukocyte Biology*, 79:1242-1251 (2006).

Pilling, D. et al., "Inhibition of Fibrocyte Differentiation by Serum Amyloid P.," The Journal of Immunology, 17(10):5537-5546 (2003).

Pilling, D., et al., "Reduction of Bleomycin-Induced Pulmonary Fibrosis by Serum Amyloid P," The Journal of Immunology, 179(6):4035-4044 (2007).

Pontet, M., et al., "One Step Preparation of Both Human C-Reactive Protein and Cit," FEBS Letters, 88(2):172-175 (1978).

Portolano et al., "Lack of Promiscuity in Autoantigen-Specific H and L Chain Combinations as Revealed by Human H and L Chain "Roulette","J. Immunol., 150(3):880-887 (1993).

Potempa, L. A., et al., "Effect of Divalent Metal Ions and pH Upon the Binding Reactivity of Human Serum Amyloid P0 Component, a C-Reactive Protein Homologue, for Zymosan," The Journal of Biological Chemistry, 260(22):12142-12147 (1985).

Prelli, F., et al., "The Primary Structure of Human Tissue Amyloid P Component From a Patient with Primary Idiopathic Amyloidosis," The Journal of Biological Chemistry, 260(24):12895-12898 (1985).

Quan et al., "The Role of Circulating Fibrocytes in Fibrosis" Current Rheumatology Reports. 8(2): 145-150 (2006).

Rudikoff et al., "Single Amino Acid Substitution Altering Antigen-Binding Specificity," Proc Natl Acad Sci USA, 79(6):1979-1983 (1982).

Russo, F. P., et al., "The Bone Marrow Functionally Contributes to Liver Fibrosis," Gastroenterology, 130(6):1807-1821 (2006).

Russo, F. P., et al., "Liver Fibrosis; Bone Marrow Functionality Contributes to Liver Fibrosis," Gastroenterology Week Jul. 31, 2006, 130(6):83-84.

Sada, K., et al., "Structure and Function of Syk Protein-Tyrosine Kinase," J Biochem, 130(2):177-186 (2001).

Saeland, E., at al., "Human C-reactive Protein Does Not Bind to FcγRIIa on Phagocytic Cells," The Journal of Clinical Investigation, 107(5):641-643 (2001).

Sawada et al., "The Ace Inhibitor, Quinapril, Ameliorates Peritoneal Fibrosis in an Encapsulating Peritoneal Sclerosis Model in Mice" Pharmacological Research. 46(6): 505-510 (2002).

Schmidt, M., et al., "Identification of Circulating Fibrocytes as Precursors of Bronchial Myofibroblasts in Asthma," The Journal of Immunology, 171(1):380-389 (2003).

Schwalbe, et al., "Pentraxin Family of Proteins Interact Specifically with Phosphorylcholine and/or Phosporylethanolamine," Biochemistry, 31:4907-1645 (1992).

Shoenfeld, Y., et al., "The Mosaic of Autoimmunity: Prediction, Autoantibodies, and Therapy in Autoimmune Diseases—2008," Israel Medical Association Journal, 10(1):13-19 (2008).

Shrive, A. K., et al., "Three Dimensional Structure of Human C-Reactive Protein," Nature Structural Biology, 3(4):346-354 (1996).

Siebert et al., "Effect of Enzymatic Desialylation of Human Serum Amyloid P Component on Surface Exposure of Laser Photo CIDNP (Chemically Induced Dynamic Nuclear Polarization)—Reactive Histidine, Tryptophan and Tyrosine Residues," *FEBS Letters*, 371(1):13-6 (1995).

Sjoblom, T., et al., "The Consensus Coding Sequences of Human Breast and Colorectal Cancers," Science, 314(5797):268-274 (2006).

Srinivasan, N., et al., "Comparative Analyses of Pentraxins: Implications for Protomer Assembly and Ligand Binding," Structure, 2(11):1017-1027 (1994).

Steel, D. M., et al., "The Major Acute Phase Reactants: C-Reactive Protein, Serum Amyloid P Component and Serum Amyloid A Protein," Immunology Today, 15(2):81-88 (1994).

Stein, M. P., et al., "C-reactive Protein Binding to FcγRIIa on Human Monocytes and Neutrophils is Allele-Specific," The Journal of Clinical Investigation, 105(3):369-376 (2000).

Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).

Sutterwala, F. S., et al., "The Taming of IL-12 Suppressing the production of Proinflammatory Cytokines," Journal of Leukocyte Biology, 65(5):543-551 (1999).

Thompson, A. R., et al., "Human Plasma P Component: Isolation and Characterization," Biochemistry, 17(20):4304-4311 (1978).

Thompson, D., et al., "The Physiological Structure of Human C-Reactive Protein and its Complex with Phosphocholine", Structure, 7(2):169-177 (1999).

Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).

Toubi, E., et al., "High Dose Intravenous Immunoglobulins: An Option in the Treatment of Systemic Lupus Erythematosus," Human Immunology, 66(4):395-402 (2005).

Tridandapani, S., et al., "Regulated Expression and Inhibitory Function of Fcγ-RIIb in Human Monocyte Cells," Journal of Biological Chemistry, The American Society for Biochemistry and Molecular Biology, Inc, 277(7):5082-5089 (2002).

Trinchieri, G., "Interleukin-12 and the Regulation of Innate Resistance and Adaptive Immunity," Nature Reviews Immunology, 3(2):133-146 (2003).

Tucci, A., et al., "Biosynthesis and Postsynthetic Processing of Human C-Reactive Protein," The Journal of Immunology, 131(5):2416-2419 (1983).

(56) References Cited

OTHER PUBLICATIONS

Turner, M., et al., "Tyrosine Kinase SYK: Essential Functions for Immunoreceptor Signalling," Immunology Today, 21(3):148-154 (2000).
Underwood, D. C., et al., "SB 239063, a p38 MAPK Inhibitor, reduces Neutrophilia, Inflammatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Wang, Q., et al., "Effect of Antibody Against Integrin α4 on Bleomycin-Induced Pulmonary Fibrosis in Mice," Biochemical Pharmacology, 60:1949-1658 (2000).
Weimann, et al., "Studies of Wound Healing: Effects of Calcium D-Panthothenate on the Migration, Proliferation and Protein Synthesis of Human Dermal Fibroblasts in Culture," Interat. J. Vit. Nutr. Res., 69(2):113-119 (1999).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Identification of Fibrocytes in Postburn Hypertrophic Scar," Wound Repair and Regeneration, 13(4):398-404 (2005).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yu, L., et al., "Therapeutic Strategies to Halt Renal Fibrosis," Current Opinion in Pharmacology, 2:177-181 (2002).
Zahedi K., "Characterization of the Binding of Serum Amyloid P To Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Barabino and Dana, "Animal Models of Dry Eye: A Critical Assessment of Opportunities and Limitations," Investigative Ophthalmology & Visual Science, vol. 45(6): 1641-1646 (2004).
Boysen, S. et al., "Recombinant human serum amyloid P component from Pichia pastoris: production and characterization," Protein Expression and Purification, vol. 35(2): 284-292 (2004).
Brasil et al., "Tear film analysis and its relation with palpebral fissure height and exophthalmos in Graves' ophthalmopathy," Arquivos Brasileiros de Oftalmologia, vol. 58(5): 615-618 (2005). (Abstract).
Garcia de Frutos et al., "Serum Amyloid P Component Binding to C4b-binding Protein," The Journal of Biological Chemistry: 270(45):26950-26955 (1995).
Heegaard, N.H.H., "Microscale characterization of the structure-activity relationship of a heparin-binding glycopeptide using affinity capillary electrophoresis and immobilized enzymes," Journal of Chromatography, vol. 853(1-2):189-195 (1999).
<http://en.wikipedia.org/wiki/Serum_amyloid_P_component> downloaded from the internet on Apr. 16, 2013.
<http://en.wikipedia.org/wiki/Pentraxins> downloaded from the internet on Apr. 16, 2013.
Hundt, M., et al., "Treatment of Acute Exacerbation of Systemic Lupus Erythematosus with High-Dose Intravenous Immunoglobulin," Rheumatology (Oxford), 39(11):1301-1302 (2000).
Ilium, Lisbeth, "Nasal Drug Delivery-possibilities, problems and solutions," Journal of Controlled Release, vol. 87(103):187-198 (2003).
Kawashima et al., Pulmonary delivery of insulin with nebulized DL-lactide/glycolide copolymer (PLGA) nanospheres to prolong hypoglycemic effect, Journal of Controlled Release, vol. 62(102): 279-287 (1999).
Pepys, M. B., et al., "Serum Amyloid P Component is the Major Calcium-Dependent Specific DNA Binding Protein of Serum," Biochemical and Biophysical Research Communications, 148(1):308-313 (1987).
Schrader et al., "Animal models of dry eye," Developments in ophthalmology, vol. 41: 298-312 (2008). (Abstract).
Siebert, Hans-Christian et al., "Comparison between intact and desialylated human serum amyloid P component by laser photo CIDNP) (chemically induced dynamic nuclear polarization) technique: An indication for a conformational impact of sialic acid," Glycoconjugate Journal, vol. 14(8):945-949 (1997).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Supplementary EP Search Report No. EP 10 75 1361 dated Dec. 7, 2012.
Samarasinghe et al., "A comparison between intratracheal and inhalation delivery of Aspergillus fumigatus conidia in the development of fungal allergic asthma in C57BL/6 mice," Fungal Biology, vol. 115: 21-29 (2011).
Sen et al., "Structural, quantitative and functional comparison of amyloid P component in sera from patients with system lupus erythematosus and healthy donors," Scandinavian Journal of Immunology, vol. 56: 645-651 (2002).
Banham et al., "FOXP3+ regulatory T cells: Current controversies and future perspectives," European Journal of Immunology, vol. 36(11):2832-2836 (2006).
Hori, Shohel, "Journal of Clinical and Experimental Medicine", vol. 227(5):294-298 (2008) (abstract).
Mascarenhas, J., "Rationale for combination therapy in myelofibrosis," Best Practice & Research Clinical Haematology, vol. 27:197-208 (2014).
Murray et al., "TGF-beta driven lung fibrosis is macrophage dependent and blocked by Serum amyloid P," The International Journal of Biochemistry & Cell Biology, vol. 43:154-162 (2011).
Nybo et al., "Isoforms of Murine and Human Serum Amyloid P Component," Scan. J. Immunol., vol. 48:350-356 (1998).
Tanaka and Sakaguchi, "Regulatory T cell and autoimmune diseases," Japanese Journal of Clinical Immunology, vol. 28(5):291-299 (2005), Abstract only.
Wells, James A., "Additivity of Mutational Effects in Proteins," Biochemistry, vol. 29:8509-8517 (1990).

\* cited by examiner

Figure 1

```
Homo sapiens      H T D L S G K V F V F P R E S V T D H V N L I T P L E K P L
Gallus gallus     Q E D L Y R K V F V F R E D P S D A Y V L L Q V Q L E R P L
Bos taurus        Q T D L R G K V F V F P R E S S T D H V T L I T K L E K P L
C. migratorius    Q T D L T G K V F V F P R E S E S D Y V K L I P R L E K P L Homo sapiens      Q N F T L C F R A Y S D L S R A Y S L F S Y N T Q G R D N E
Gallus gallus     L N F T V C L R S Y T D L T R P H S L F S Y A T K A Q D N E
Bos taurus        K N L T L C L R A Y S D L S R G Y S L F S Y N I H S K D N E
C. migratorius    E N F T L C F R T Y T D L S R P H S L F S Y N T K N K D N E Homo sapiens      L L V Y K E R V G E Y S L Y I G R H K V T S K V I E K F P A
Gallus gallus     I L L F K P K P G E Y R F Y V G G K Y V T F R V P E N R G E
Bos taurus        L L V F K N G I G E Y S L Y I G K T K V T V R A T E K F P S
C. migratorius    L L I Y K E R M G E Y G L Y I E N V G A I V R G V E E F A S Homo sapiens      P V H I C V S W E S S S G I A E F W I N G T P L V K K G L R
Gallus gallus     W E H V C A S W E S G S G I A E F W L N G R P W P R K G L Q
Bos taurus        P V H I C T S W E S S T G I A E F W I N G K P L V K R G L K
C. migratorius    P V H F C T S W E S S S G I A D F W V N G I P W V K K G L K Homo sapiens      Q G Y F V E A Q P K I V L G Q E Q D S Y G G K F D R S Q S F
Gallus gallus     K G Y E V G N E A V V M L G Q E Q D A Y G G G F D V Y N S F
Bos taurus        Q G Y A V G A H P K I V L G Q E Q D S Y G G G F D K N Q S F
C. migratorius    K G Y T V K T Q P S I I L G Q E Q D N Y G G G F D K S Q S F Homo sapiens      V G E I G D L Y M W D S V L P P E N I L S A Y Q G T P L P A
Gallus gallus     T G E M A D V H L W D A G L S P D K M R S A Y L A L R L P P
Bos taurus        M G E I G D L Y M W D S V L S P E E I L L V Y Q G S S S I S
C. migratorius    V G E M G D L N M W D S V L T P E E I K S V Y E G S W L E P Homo sapiens      N I L D W Q A L N Y E I R G Y V I I K P L V W V
Gallus gallus     A P L A W G R L R Y E A K G D V V V K P R L R E A L G A
Bos taurus        P T I L D W Q A L K Y E I K G Y V I V K P M V W G
C. migratorius    N I L D W R A L N Y E M S G Y A V I R P R V W H
```

TREATMENT METHODS FOR HYPERSENSITIVE DISORDERS

CROSS-REFERENCE TO RELATED APPLICATIONS

This application claims the benefit of U.S. Provisional Application Ser. No. 61/209,795 filed Mar. 11, 2009. All the teachings of the above-referenced application is incorporated herein by reference.

SEQUENCE LISTING

The instant application contains a Sequence Listing which has been submitted via EFS-Web and is hereby incorporated by reference in its entirety. Said ASCII copy, created on Apr. 30, 2010, is named 10411212.txt and is 7,538 bytes in size.

BACKGROUND OF THE INVENTION

Native CD4 T-cells can differentiate upon activation into either Th1 or Th2 cells, which have significantly different immune functions based on the cytokines they produce. Th1 cells promote type 1 immunity, producing IFN-γ which drives cell-mediated immunity and $IgG_{2A}$ synthesis. Th2 cells enhance type 2 immunity by producing IL-4, IL-5, and IL-13 and promoting antibody-mediated responses and class switching to $IgG_1$ and IgE. These immune responses can be detrimental when they are not appropriately regulated, as in autoimmune diseases, or when excessive, as in allergic diseases.

The Th1 differentiation pathway is normally stimulated in response to infectious microbes that activate macrophages and/or NK cells. These include bacteria, some parasites, viruses and certain foreign antigens. A common feature of these antigens is that they elicit innate immune reactions with the production of IL-12. IL-12 binds to receptors on antigen-stimulated CD4+ cells and activates the transcriptional factor STAT-4. Subsequently, STAT-4 promotes the differentiation of the T-cells into Th1 cells. A transcription factor called T-bet also plays a critical role in Th1 development. T-bet is induced by IFN-α and provides an amplification of the Th1 responses. Th1 cells secrete IFN-γ, lymphotoxin (LT), and TNF. IFN-γ acts on macrophages to increase phagocytosis and promote killing of microorganism in phagolysomes and on B lymphocytes to stimulate production of IgG antibodies that opsonize microbes and other antigens for phagocytosis. LT and TNF activate neutrophils and stimulate inflammation. IL-2 is an autocrine growth factor made by Th1 cells.

Th2 differentiation normally occurs in response to helminths and allergens. Host response to these antigens can cause chronic T-cell stimulation, often without a significant innate immune response or macrophage activation. The differentiation of antigen-stimulated T-cells to the Th2 subset is dependent on IL-4, which functions by activating STAT-6. STAT-6, similar to STAT-4, is a transcriptional factor that stimulates Th2 development. Another transcription factor called GATA-3 also plays an important role in Th2 development by activating transcription of Th2-specific cytokine genes. Th2 cells secrete IL-4 and IL-5. IL-4 acts on B-cells to stimulate production of antibodies that bind to mast cells, such as IgE. IL-4 is also an autocrine growth and differentiation cytokine for Th2 cells. IL-5 activates eosinophils, primarily a defense against parasitic infections. Th2 cytokines also inhibit both classical macrophage activation and Th1-mediated reactions.

Allergy is classified as a Type I hypersensitivity reaction, also known as an immediate-type hypersensitivity reaction, and is stimulated by Th2-mediated production of IgE. Th2 cells can promote antibody isotype switching of B-cells from IgM to IgE. IgE can be produced by plasma cells located in the lymph nodes draining from the site of antigen entry or peripherally produced at the local site of allergic reaction. IgE sensitizes mast cells and basophils by binding to the high-affinity receptor for IgE (FcεRI) expressed on their surface. Upon allergen-mediated crosslinking of the IgE-FcεR1 complex, mast cells and basophils degranulate to release vasoactive amines (primarily histamine), lipid mediators (prostaglandins and cysteinyl leukotrienes), cytokines and chemokines, all of which characterize the immediate phase of the allergic reaction. Histamine is one of the key factors of the immediate phase of the allergic reaction, regulating dendritic cells, T cells and antibody isotype class-switching via four distinct histamine receptors (HR). HR2 acts as an anti-inflammatory and anti-allergic receptor, whereas HR1, HR3 and HR4 show proinflammatory effects. Mast cells are not only associated with type-I hypersensitivity reactions but also play a role in chronic inflammation. IgE also binds FcεR1 on the surface of dendritic cells and monocytes and binds FcεRII on the surface of B-cells. These interactions enhance the uptake of allergens by these antigen-presenting cells and the subsequent presentation of allergen-derived peptides to specific CD4+ T-cells, which drive the late phase of the allergic reaction. Treatment with anti-IgE monoclonal antibody significantly reduces allergen-induced late-phase responses, demonstrating the role of IgE in enhancing T-cell responses to allergens.

After allergen exposure, increased levels of histamine and tryptase can be detected in the bronchoalveolar lavage in allergic-asthma, in nasal washes in rhinitis, in tears in conjunctivitis and the circulatory system in systemic anaphylaxis. In the lower airways, the primary targets for mast cell mediators are the secretory glands, blood vessels, and bronchial smooth muscle. Bronchoconstriction is the main clinical manifestation of early phase responses in allergic-asthma, manifested by a decrease in forced expiratory volume in 1 second ($FEV_1$) within 1 hour of allergen exposure. In the nasal mucosa, the potential targets for mast cell mediators are the mucus glands, nerves, blood vessels, and venous sinuses. The clinical manifestation of early phase responses in the upper airway are itching, sneezing, nasal obstruction, and watery discharge. Typically early phase responses resolve within an hour.

The late phase response develops as a result of cytokines and chemokines generated by resident inflammatory cells, such as mast cells, macrophages, and eosinophils. Although mast cells are not essential for the late phase response, the detection of IL-5, IL-6, IL-13 and TNF-α in mast cells, and their release after the cross-linking of IgE supports roles for both IgE and mast cells in ensuring persistent allergic inflammation and hyperresponsiveness. In chronic allergic inflammations of lung and skin, the subepithelial tissue turns into a secondary lymphoid organ-like tissue with the infiltration of T-cells, dendritic cells and B-cells. Activated T-cells interact with resident tissue cells as well as with other migrating inflammatory cells. They activate bronchial epithelial cells, smooth muscle cells, macrophages, fibroblasts in the chronic-asthmatic lungs, and epidermal keratinocytes in the allergic skin Resident tissue cells contribute to inflammation by secretion of pro-inflammatory cytokines and chemokines. Production of IFN-γ and TNF-α together with expression of FAS-ligand by Th1 cells leads to epithelial cell activation followed by apoptosis, and compromises barrier function of epithelial cells in the lungs and the skin. This involves two stages. First, the pro-inflammatory stage with activation of epithelial cells and the release of chemokines and pro-inflammatory cytokines. This is followed by the eventual death of keratinocytes and bronchial epithelial cells, which leads to a visible pathology including epithelial desquamation in chronic-asthma and epidermal spongiosis in eczema.

Antibody-mediated destruction of host cells is an uncommon side-effect associated with in the intake of certain drugs, such as the antibiotic penicillin These are Type II hypersensitivity reactions in which the drug binds to the cell surface and serves as a target for anti-drug IgG antibodies and subsequently promote destruction of the cell. The anti-drug antibodies are only produced in a minority of the population, and it is not well understood why these antibodies are generated in these individuals. The cell-bound antibody triggers clearance of the cell from the circulation, predominantly by tissue macrophages in the spleen, which bear Fcγ receptors.

Type III hypersensitivity reactions can arise with soluble antigens. The pathology is caused by the deposition of antigen-antibody aggregates or immune complexes within particular tissues and organ sites Immune complexes are generated in all antibody responses but their pathogenic potential is determined, in part, by their size, and the amount, affinity, and isotype of the responding antibody. Larger aggregates fix complement and are readily cleared from the circulation by the mononuclear phagocyte system. However, small complexes that form tend to deposit in blood vessels walls. There they can ligate Fc receptors on leukocytes, leading to leukocyte activation and tissue injury.

Type IV hypersensitivity reactions are usually stimulated by soluble antigens and result in chronic inflammatory disorders, like chronic-asthma and chronic allergic rhinitis. An important feature of asthma is chronic inflammation of the airways, which is characterized by the continued presence of increased numbers of Th2 lymphocytes, eosinophils, neutrophils, and other leukocytes. These cells stimulate increased mucus secretion. The direct action of Th2 cytokines such as IL-9 and IL-13 on airway epithelial cells may have a role on the induction of goblet-cell metaplasia and the secretion of mucus.

Most immediate hypersensitivity disorders are associated with excessive Th2 responses to normally innocuous environmental antigens. These disorders predominate in most industrial countries and are a growing healthcare concern in developing nations. There are numerous medicaments to treat or alleviate the symptoms associated hypersensitive diseases, including systemic therapies as well as more localized treatments. Local therapeutics are most often prescribed to achieve the maximum effect at the site of disease while minimizing the possibility of systemic side-effects. These local treatments are generally administered topically or by aerosol/spray, including alpha-adrenergic decongestants, adrenergic bronchodilators, antihistamines, and corticosteroids. Unfortunately, many of these drugs still have the disadvantage of producing unwanted side-effects even when administered locally. As many patients use excessive quantities of these drugs to relieve symptoms quickly, there is an increased risk that the patient will suffer deleterious effects. Therefore, a need remains for developing more effective treatments for the underlying causes of hypersensitivity responses.

SUMMARY OF THE INVENTION

In part, the disclosure demonstrates that SAP and SAP agonists are useful in the treatment of hypersensitivity disorders. One aspect of the invention provides methods for treating, inhibiting or reducing the severity of a hypersensitivity disorder in a patient in need thereof by administering a therapeutically effective amount of an SAP agonist. The administration of an SAP agonist may delay the development of a hypersensitivity disorder, reduce the number of days a patient is afflicted with a hypersensitivity disorder, and/or reduce the severity of a hypersensitivity disorder. The disclosure provides methods for treating patients afflicted with a hypersensitivity disorder, as well as patients at risk of developing a hypersensitive disorder. In some embodiments, the administration of an SAP agonists may commence prior to, concurrently with, or after treatments that may place patients at risk for developing a hypersensitivity disorder. In certain embodiments, SAP and SAP agonists are useful in treating a hypersensitivity disorder before the onset of fibrosis.

The disclosure further provides methods for treating, inhibiting or reducing the severity of a hypersensitivity disorder in the respiratory system of a patient by administration of a therapeutically effective amount of an SAP agonist. The administration of an SAP agonist may delay the development of a respiratory hypersensitivity disorder, reduce the number of days a patient is afflicted with a respiratory hypersensitivity disorder, and/or reduce the severity of a respiratory hypersensitivity disorder. In certain embodiments, SAP and SAP agonists are used to treat allergic-asthma responses. In other embodiments, SAP and SAP agonists are used to treat acute allergic-asthma responses before the onset of chronic-asthma disease. In certain embodiments, the hypersensitivity disorder treated is not asthma. In certain embodiments, the hypersensitivity disorder treated is not chronic-asthma.

The disclosure further provides methods for treating, inhibiting or reducing the severity of a hypersensitivity disorder in a patient by administering a composition that includes an SAP agonist and an additional active agent. In some embodiments, the additional active agent may be selected from the group of anti-IgE antibodies, Th1 agonist, Th2 antagonists, short and long term beta-agonists, corticosteroids, cromolyn, xanthines, and allergen-specific immunotherapy. In some embodiments, the active agent may be an inhibitor of mast cells, histamine, prostaglandins, chemokines, Th1- and Th2-associated mediators, and cysteinyl leukotrienes. Administration of the composition to a patient may delay the development of a hypersensitivity disorder, reduce the number of days a patient is afflicted with a hypersensitivity disorder, and/or reduce the severity of a hypersensitivity disorder.

The disclosure additionally provides a kit for the treatment of a hypersensitivity disorder in a patient. The kit comprises one or more SAP agonists that may be formulated to be conjointly administered. In some embodiments, the SAP agonist is formulated to be administered conjointly with an additional active agent.

Hypersensitivity disorders that can be treated as part of the invention include allergic rhinitis, allergic sinusitis, allergic conjunctivitis, allergic-asthma, atopic eczema, dermatitis, urticaria, anaphylaxis, food allergies, allergic reactions to venom of stinging insects, allergic bronchoconstriction, allergic dyspnea, allergic increase in mucus production in lungs, pneumonitis, psoriasis, and/or other Th2-mediated hyper-responsive disorders. In certain aspects, anti-hypersensitivity compositions of the disclosure maybe used to treat, prevent, or reduce the severity of an inflammatory eye disease including, for example, dry eye diseases, allergic conjunctivitis, uveitis, and uveoretinitis as well as eye inflammation associated with corneal transplant, neoplastic disorders, and congenital disorders.

The disclosure provides SAP agonists useful in the methods of the invention. SAP agonists may be administered topically, by injection, by intravenous injection, by inhalation, continuous release by depot or pump, and in any combination. SAP agonists may increase or mimic SAP signaling, increase SAP activity, increase SAP expression, or increase SAP levels in serum. A SAP agonist may be a small molecule, nucleic acid, or polypeptide. In some embodiments, the SAP agonist is an SAP polypeptide, an anti-FcγRI antibody, an anti-FcγRII antibody, an anti-FcγRIII antibody, a cross-linked anti-FcγR antibody, an aggregated IgG antibody, or a cross-linked IgG antibody. The SAP agonist may be formulated to be administered conjointly with one or more SAP agonists or other active agents.

The disclosure further comprises methods for treating or preventing a hypersensitivity disorder or condition in a patient using regulatory T cells. The method comprises obtaining a sample containing T cells, contacting the T cell sample with an SAP agonist in an ex vivo culture to produce a population of cells enriched for regulatory T cells, isolating the regulatory T cells, and administering a therapeutically effective amount of the isolated regulatory T cells to the patient to treat or prevent a hypersensitivity disorder or condition. In some embodiments, the regulatory T cells are FoxP3$^+$ and/or IL-10 producing regulatory T cells. The SAP agonist may promote regulatory T cell-mediated suppression of the hypersensitivity disorder or condition. The administration of regulatory T cells may inhibit the onset of a hypersensitivity disorder or condition, reduce the number of days a patient is afflicted with a hypersensitivity disorder or condition, and/or reduce the severity of a hypersensitivity disorder or condition. The disclosure provides methods for treating both patients afflicted with a hypersensitivity disorder, as well as patients at risk of developing a hypersensitivity disorder. In some embodiments, the administration of regulatory T cells may commence prior to, concurrently with, or after treatments that may place patients at risk for developing a hypersensitivity disorder. In some embodiments, the regulatory T cells are administered on a periodic basis. In certain aspects, regulatory T cells are useful in treating a hypersensitivity disorder before the onset of fibrosis. In some embodiments, the patient is administered at least one additional active agent. In certain aspects, the additional active agent is a therapeutic agent used to treat or prevent the hypersensitivity disorder. In certain aspects, the additional active agent is an SAP agonist. In certain aspects, the additional active agent is a cytokine. Cytokines useful in the methods of the present invention include, but are not limited to, IL-2, IL-4, IL-10, TGF-β, IL-15 and/or IL-17. In some embodiments, the additional active agent is administered on a periodic basis.

BRIEF DESCRIPTION OF THE DRAWINGS

FIG. 1. Amino acid sequence alignment of human (SEQ ID NO: 1, amino acids 20-223 of Genbank Accession No. NP_001630), *Gallus gallus* (SEQ ID NO: 2, amino acids 20-227 of Genbank Accession No. NP_001034653), *Bos taurus* (SEQ ID NO: 3, amino acids 20-224 of Genbank Accession No. AAI02624), and *Cricetulus migratorius* (SEQ ID NO: 4, amino acids 20-223 of Genbank Accession No. AAB28726), serum amyloid P polypeptides (signal sequence not depicted). Amino acids identical to the human SAP are shaded.

DETAILED DESCRIPTION OF THE INVENTION

Overview

Figure 2A:
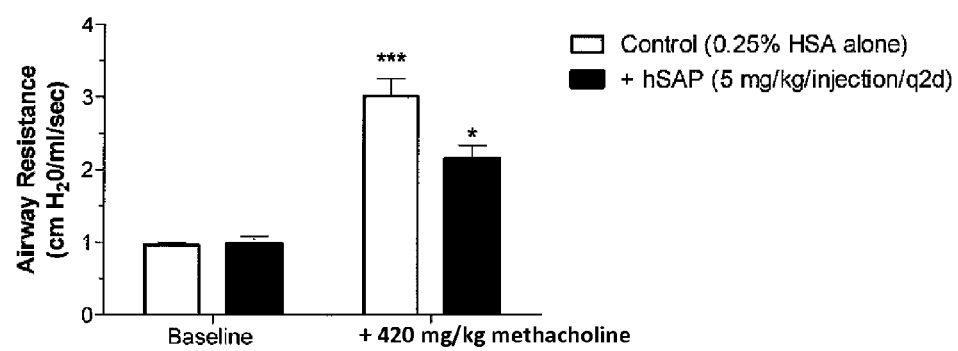
FIGS. 2A and 2B. Exogenous SAP therapy prevented and reversed established airway hyperresponsiveness in a fungal asthma model. *A. fumigatus*-sensitized and conidia-challenged C57BL/6 mice received PBS, or hSAP via intraperitoneal injection every other day from days 0-15 (FIG. 2A) or 15-30 (FIG. 2B) after conidia, and airway resistance was measured following methacholine challenge using invasive airway resistance analysis (Buxco). Data are mean±SEM, n=5 mice/group. *P<0.05, ***P<0.001 compared with baseline airway resistance in the appropriate treatment group.

The current standard of care for the treatment of allergic airway diseases includes short and long acting beta-agonists, and inhaled or systemic corticosteroids cromylin and xanthines that all have the potential of detrimental side-effects. The present disclosure describes a new mechanistic protein-based therapeutic approach for the treatment of allergic airway disease and diseases associated with excessive Th2 pathology. The present disclosure relates to the surprising discovery that serum amyloid P (SAP) demonstrates a therapeutic affect in the treatment of hypersensitivity disorders.

Serum amyloid P ("SAP") is a naturally-occurring serum protein in mammals composed of five identical subunits or protomers which are non-covalently associated in a disc-like molecule. SAP is a 125,000 Dalton pentameric glycoprotein composed of five, non-covalently linked, 25,000 Dalton protomers. SAP belongs to the pentraxin superfamily of proteins, characterized by this cyclic pentameric structure. The classical short pentraxins include SAP as well as C-reactive protein. (Osmand, A. P., et al., Proc. Nat. Acad. Sci., 74:739-743 (1977)) It is synthesized in the liver and the physiological serum half-life of human SAP in humans is 24 hours. The sequence of the human SAP subunit is depicted in SEQ ID NO: 1 (amino acids 20-223 of Genbank Accession No. NP_001630, signal sequence not depicted). Previous work has demonstrated SAP binds to Fc receptors for IgG (FcγR). SAP binding to FcγR provides and inhibitory signal for fibrocyte, fibrocyte precursor, myofibroblast precursor, and/or hematopoetic monocyte precursor differentiation.

Definitions

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a hypersensitive disorder and/or adverse affect attributable to the disorder. "Treatment", as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "inhibits" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "subject" and "patient" refer to animals including mammals including humans. The term "mammal" includes primates, domesticated animals including dogs, cats, sheep, cattle, goats, pigs, mice, rats, rabbits, guinea pigs, horses, captive animals such as zoo animals, and wild animals.

As used herein, the term "tissue" refers to an organ or set of specialized cells such as skin tissue, lung tissue, kidney tissue, nasal passage, throat and other types of cells.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

As used herein the term "hypersensitivity diseases" refers to disorders caused by the host immune responses. Hypersensitivity diseases include allergic-immune diseases that result from uncontrolled or excessive responses against foreign antigens, such as microbes and allergens. Hypersensitivity reactions have been classified into four categories (Types I-IV) based on the underlying immunological mechanism of the response. Most hypersensitivity responses (Types I-III) are mediated by antibodies, and these reactions can be distinguished by the different types of antigens recognized and by classes of antibody involved. Type I responses are mediated by IgE, a potent inducer of mast-cell activation. Type II and III responses are mediated by IgG, which can engage complement-mediated and phagocytic effector mechanisms depending on the subclass of IgG and the nature of the antigen. Type II responses are directed against cell-surface or matrix antigens. A special category of Type II responses involves IgG antibodies against cell-surface receptors that disrupt the normal functions of the receptor, either by causing uncontrollable activation or by blocking receptor function. In Type III responses, antibodies bind soluble antigens and form immune-complexes. These antigen-antibody complexes can precipitate and deposit within various host organ and tissue sites, particularly in the spleen and liver. The tissue damage caused by Type III responses is triggered by recognition of immune-complex on the surface of host cells. Type IV hypersensitivity reactions are T-cell mediated and can be subdivided into three groups. In the first group, activation of macrophages by Th1 cells causes an inflammatory response that results in tissue damage. In the second group, damage is caused by a Th2-mediated inflammatory response in which eosinophils predominate. In the third group, host tissue damage is caused directly by cytotoxic T-cells.

As used herein the term "immediate hypersensitivity" is defined as the type of immune reaction responsible for allergic diseases that is dependent on IgE plus antigen-mediated stimulation of tissues, and mast cells, and basophils. During the immediate hypersensitivity response, mast cells and basophils release mediators that cause increased vascular permeability, vasodilatation, bronchial and visceral smooth muscle contraction, and local inflammation.

As used herein the term "allergic-asthma response" refers to an acute airway inflammatory response in an asthmatic patient. Allergic-asthma is characterized by reversible airflow limitation and airway hyperresponsiveness. These responses are typically stimulated by normal allergen-response mechanisms mediated by Th2 CD4+ T-cell activation and subsequent Th2 cytokine production. However, airway-associated allergic responses are typically more severe with an acute onset in patients with asthma than is observed in non-asthmatic patients. In particular, IL-4, IL-5, IL-9, and IL-13 are critically important in acute allergic-asthma responses, inducing eosinophil-, macrophage-, and lymphocyte-mediated inflammatory responses, mucus hypersecretion, and airway hyperresponsiveness.

As used herein patients with "chronic asthma" are defined as patients having structural changes within their lungs as a consequence of long-term, persistent asthma responses. The structural changes include airway smooth muscle hypertrophy and hyperplasia, collagen deposition to sub-epithelial basement membranes, hyperplasia of goblet cells, thickening of airway mucosa, an increase in vascularity, and fibrosis. Tissue remodeling during chronic-asthma results in airway obstruction that is not fully reversible and therefore leads to progressive loss of lung function over time.

As used herein the term "respiratory system" refers to the anatomical features of a mammal that facilitate gas exchange gaseous external environment and the blood. The respiratory system can be subdivided into an upper respiratory tract and a lower respiratory tract based on anatomical features. The upper respiratory tract includes the nasal passages, pharynx and the larynx. While the trachea, the primary bronchi and lungs are parts of the lower respiratory tract. The respiratory system can also be divided into physiological, or functional, zones. These include the conducting zone (the region for gas transport from the outside atmosphere to just above the alveoli), the transitional zone, and the respiratory zone (the alveolar region where gas exchange occurs).

As used herein, the term "nucleic acid" refers to polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The terms "compound", "test compound", and "active agent" are used herein interchangeably and are meant to include, but are not limited to, polypeptides, nucleic acids, small molecules and antibodies. "Small molecule" as used herein, is meant to refer to a molecule that has a molecular weight of less than about 5 kD and most preferably less than about 2.5 kD, or even less than 1 kD. Small molecules can be nucleic acids, peptides, polypeptides, peptidomimetics, carbohydrates, lipids or other organic (carbon-containing) or inorganic molecules (including, but not limited to, metals and organometallic compounds). Many pharmaceutical companies have extensive libraries of chemical and/or biological mixtures comprising arrays of small molecules, often fungal, bacterial, or algal extracts, which can be screened with any of the assays of the disclosure.

Treatment Methods

One aspect of the disclosure provides methods for treating, inhibiting, or reducing the severity of a hypersensitivity disorder in a patient, where the methods include administering a therapeutically effective amount of an SAP agonist to a patient in need thereof. In some embodiments, administration of an SAP agonist reduces the number of days a patient is afflicted with a hypersensitivity disorder by at least 1, 2, 3, 4, 5, 6, 7, 8, 9, 10, 15 or more days. In some embodiments, administration of an SAP agonist inhibits the onset of a hypersensitivity disorder in a patient by at least 1, 2, 3, 4, 5, 6, 7, 8, 9, 10, 15 or more days.

While the methods of the invention can be used to treat patients afflicted with a hypersensitivity disorder, in some embodiments, the methods are also carried out with patients who do not have, but are at risk of developing a hypersensitivity response. In patients at risk of developing a hypersensitivity disorder, treatment according to the invention can reduce the severity, inhibit the development, or prevent the onset of a hypersensitivity response. In some embodiments, administration of an SAP agonist reduces the number of days a patient is afflicted with a hypersensitivity disorder by at least 1, 2, 3, 4, 5, 6, 7, 8, 9, 10, 15 or more days. In some embodiments, administration of an SAP agonist inhibits the onset of a hypersensitivity disorder in a patient by at least 1, 2, 3, 4, 5, 6, 7, 8, 9, 10, 15 or more days.

In certain methods of the invention, an SAP agonist is administered to a patient before, during, and/or after treatment with a therapy that causes a hypersensitivity response or puts a patient at risk of developing such a disorder. In certain embodiments, the anti-hypersensitivity therapy may be used to treat allergy-specific immune responses, such as anaphylaxis, to various antigens, including, but not limited to, antimicrobials, anticonvulsants, chemotherapeutics, heparin, insulin, protamine, aspirin and other non-steroidal anti-inflammatory drugs, muscle relaxants, induction agents, narcotics, colloids for intravascular volume expansion, radiocontrast materials, blood products, and latex.

Another aspect of the disclosure provides methods for treating hypersensitivity disorders by conjoint administration of multiple SAP agonists. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in separate formulations, either concomitantly or sequentially. Thus, an individual who receives such treatment can benefit from a combined effect of different therapeutic compounds.

Another aspect of the application provides methods for treating hypersensitivity-related disorders by conjoint administration of one or more SAP agonists and an additional active agent. In some embodiments, anti-hypersensitivity therapy encompasses agents that inhibit or antagonize pro-hypersensitivity factors, such as agents that antagonize one or more growth factors or cytokines involved in the formation and maintenance of a hypersensitivity response. In this manner, anti-hypersensitivity therapy may be used to antagonize the activities of cells involved in hyperresponsiveness including Th2 T-cells, mast cells, basophils, B-cells (plasma), eosinophils, macrophages, and dendritic cells.

In some embodiments, the active agent is a pro-hypersensitivity factor antagonist and/or anti-hypersensitivity agent. In certain embodiments, the pro-hypersensitivity factors that are targets for antagonists as part of the therapy of the present invention may include, without limitation, IL-4, IL-13, IL-5, IL-19, IL-15, IL-17A, IL-17E, IL-33, IL-21, TSLP, IgE, histamine, allergic prostaglandins, cysteinyl leukotrienes, thrombin, angiotensin, endothelin, PAF and other factors known to promote or maintain hypersensitivity disorders. In certain embodiments, the active agent may include antibodies directed to one or more pro-hypersensitivity factors.

In some embodiments, the active agent may include antagonists of the corresponding receptor of one more of the pro-hypersensitivity factors and/or cytokines, such as fragments thereof.

In certain embodiments, the active agent may include inhibitors of receptor signaling pathways required for immune effector cell activation/proliferation, release of inflammatory mediators oxidative burst, phagocytosis and antigen presentation.

In certain embodiments, the active agent may include one or more oligonucleotides that contain at least one sequence that is antisense with respect to one or more of the pro-hypersensitivity factors and/or cytokines.

In other selected embodiments, the active agent may include inhibitors of precursor molecules for histamine, prostaglandins, and cysteinyl leukotrienes.

In certain embodiments, the active agent may be selected from the group consisting of corticosteroids, long- and short-acting β2 agonists, cromolyn and/or xanthines.

In some embodiments the active agent includes one or more IL-10, IL-12, and/or IFN-γ agonists.

In certain embodiments, a SAP agonist for the treatment of a hypersensitivity related disorder is administered conjointly with allergen-specific immunotherapy (SIT).

Another aspect of this disclosure provides kits for treating hypersensitivity related disorders that compromise one or more SAP agonists. In some embodiments, the kit may include an additional active agent to be administered conjointly with one or more SAP agonists. The agonist(s) and active agent are formulated to be administered conjointly. The compounds may be administered separately or in a combined formulation. The compounds may be administered simultaneously or at different dosing schedules.

In some embodiments, the SAP agonist is selected from a small molecule, nucleic acid, or polypeptide. The SAP agonist may increase SAP signaling, mimic SAP signaling, increase SAP activity, increase SAP expression, or increase serum SAP levels. In certain embodiments, the SAP agonist is a SAP polypeptide, an FcγR antibody (anti-FcγRI, anti-FcγRII, anti-FcγRIII), an aggregated IgG antibody, or a cross-linked IgG antibody.

In some embodiments, administration of an SAP agonist is used to treat hypersensitivity disorders that include allergic rhinitis, allergic sinusitis, allergic conjunctivitis, allergic-asthma, atopic eczema, dermatitis, anaphylaxis, food allergies, allergic-asthma, atopic eczema, dermatitis, urticaria, anaphylaxis, food allergies, allergic reactions to venom of stinging and/or biting insects, allergic bronchoconstriction, allergic dyspnea, allergic increase in mucus production in lungs, pneumonitis and exacerbated COPD or other lung disease cause by acute inflammatory response to allergens (e.g., pollen, viral particles, and fungi).

In certain embodiments, administration of an SAP agonist is used to treat a hypersensitivity disorder wherein the hypersensitivity disorder is not fibrosis.

In certain embodiments, administration of an SAP agonist is used to treat allergic-asthma responses in a patient wherein the patient does not have chronic asthma.

In one aspect, the present disclosure provides methods for producing a population of cells enriched for regulatory T cells from a sample containing T cells. In some embodiments, the methods for producing a population of cells enriched for regulatory T cells are effected in vivo. In some embodiments, the method comprises obtaining a sample from a mammalian subject that comprises T cells (e.g., CD4+ cells) and contacting the T cells with SAP for a period of time sufficient to generate regulatory T cells. In some embodiments, the T cells are isolated from the mammalian sample prior to exposure to SAP. In some embodiments, the regulatory T cells are isolated from the other cells in the culture after exposure to SAP. In some embodiments, a patient is administered SAP prior to obtaining a biological sample that contains T cells from the patient.

The term "isolated" with respect to T cells refers to cell population preparation in a form that has at least 70, 80, 90, 95, 99, or 100% T cells. In some embodiments, these T cells may be 70, 80, 90, 95, 99, or 100% FoxP3$^+$ and/or IL-10 producing regulatory T cells. In some aspects, a desired cell population is isolated from other cellular components, in some instances to specifically exclude other cell types that may "contaminate" or interfere with the study of the cells in isolation. It is to be understood, however, that such an "isolated" cell population may incorporate additional cell types that are necessary for cell survival or to achieve the desired results provided by the disclosure. For example, antigen presenting cells, such as monocytes (macrophages) or dendritic cells, may be present in an "isolated" cell population of T cells or added to a population of isolated T cells for generation of regulatory T cells. In some aspects, these antigen presenting cells may be activated monocytes or dendritic cells. In some aspects the antigen presenting cells are activated by exposure to a stimulating antigen and/or SAP agonist.

Mammalian T cells for use in the methods of the disclosure may be isolated from a biological sample taken from a mammalian subject. The sample may originate from a number of sources, including, but not limited to peripheral blood, leukapheresis blood product, apheresis blood product, bone marrow, thymus, tissue biopsy, tumor, lymph node tissue, gut associated lymphoid tissue, mucosa associated lymphoid tissue, cord blood, liver, sites of immunologic lesions (e.g., synovial fluid), pancreas, and cerebrospinal fluid. The donor subject is preferably human, and can be fetal, neonatal, child, adult, and may be normal, diseased, or susceptible to a disease of interest. In some embodiments, the mammal is administered SAP prior to isolating the biological sample.

In some embodiments, the T cell sample comprises peripheral blood mononuclear cells (PBMCs) from a blood sample. By "peripheral blood mononuclear cells" or "PBMCs" is meant lymphocytes (including T-cells, B-cells, NK cells, etc.) and monocytes. In general, PBMCs are isolated from a patient using standard techniques. In some embodiments, only PBMCs are taken, either leaving or returning substantially all of the red blood cells and polymorphonuclear leukocytes to the donor. PBMCs may be isolated using methods known in the art, such as leukopheresis. In general, a 5 to 7 liter leukopheresis step is performed, which essentially removes PBMCs from a patient, returning the remaining blood components. Collection of the sample is preferably performed in the presence of an anticoagulant (e.g., heparin).

The T cell-containing sample comprising PBMCs or isolated T cells can be pretreated using various methods before treatment with SAP or an SAP agonist. Generally, once collected, the cells can be additionally concentrated, if this was not done simultaneously with collection or to further purify and/or concentrate the cells. For example, PBMCs can be partially purified by density gradient centrifugation (e.g., through a Ficoll-Hypaque gradient). Cells isolated from a donor sample are normally washed to remove serum proteins and soluble blood components, such as autoantibodies, inhibitors, etc., using technique(s) well known in the art. Generally, this involves addition of physiological media or buffer, followed by centrifugation. This may be repeated as necessary. The cells can then be counted, and in general, from $1\times10^9$ to $2\times10^9$ white blood cells are collected from a 5-7 liter leukapheresis. The purified cells can be resuspended in suitable media or buffer to maintain viability. Suitable solutions for resuspension will generally be a balanced salt solution (e.g., normal saline, PBS, Hank's balanced salt solution, etc.) optionally supplemented with fetal calf serum, BSA, HSA, normal goat serum, and/or other naturally occurring factors, in conjunction with an acceptable buffer at low concentration, generally from 5-50 mM. Convenient buffers include, but are not limited to HEPES, phosphate buffers, lactate buffers, etc.

A specific cell type (e.g., effector T cells, regulatory T cells, etc.) can be separated from a complex mixture of cells using techniques that enrich for cells having the desired characteristic (e.g., CD4+, FoxP3+, etc.). Most standard separation methods use affinity purification techniques to obtain a substantially isolated cell population. Techniques for affinity separation may include, but are not limited to, magnetic separation (e.g., using antibody-coated magnetic beads), affinity chromatography, cytotoxic agents joined to a monoclonal antibody (e.g., complement and cytotoxins), and "panning" with antibody attached to a solid matrix. Techniques providing accurate separation include fluorescence activated cell sorting, which can have varying degrees of sophistication, such as multiple color channels, impedance channels, etc. The living cells may be selected against dead cells by employing dyes that associate with dead cells (e.g., propidium iodide, LDS, etc.). Any technique may be used that is not unduly detrimental to the viability of the selected cells.

The affinity reagents used may be specific receptors or ligands for cell surface molecules (e.g., CD4, CD25, etc.). Antibodies may be monoclonal or polyclonal and may be produced by transgenic animals, immunized animals, immortalized B-cells, and cells transfected with DNA vectors encoding the antibody. Details of the preparation of antibodies and their suitability for use as specified binding members are well-known to those skilled in the art. In addition to antibody reagents, peptide-MHC antigen and T cell receptor pairs may be used, as well as peptide ligands, effector and receptor molecules.

Antibodies used as affinity reagents for purification are generally conjugated with a label for use in separation. Labels may include magnetic beads (which allow for direct separation), biotin (which can be removed with avidin or streptavdin bound to a support), fluorochromes (which can be used with a fluorescence activated cell sorter), or other such labels that allow for ease of separation of the particular cell type. Fluorochromes may include phycobiliproteins, such as phycoerythrin and allophycocyanins, fluorescein and Texas red. Frequently, each antibody is labeled with a different fluorochrome to permit independent sorting for each marker.

For purification of a desired cell population, cell-specific antibodies are added to a suspension of cells and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody (i.e., using a saturating amount of antibody). The appropriate concentration can also be determined by titration. The medium in which the cells are separated will be any medium that maintains the viability of the cells. A preferred medium is phosphate buffered saline containing from 0.1% to 0.5% BSA. Various media are commercially available and may be used according to the nature of the cells, including Dulbecco's Modified Eagle Medium, Hank's Basic Salt Solution, Dulbecco's phosphate buffered saline, RPMI, Iscove's medium, PBS with 5 mM EDTA, etc., optionally supplemented with fetal calf serum, BSA, HSA, etc.

The staining intensity of cells can be monitored by flow cytometry, where lasers detect the quantitative levels of fluorochrome (which is proportional to the amount of cell surface antigen bound by the antibodies). Flow cytometry, or fluorescent activated cell sorting (FACS), can also be used to separate cell populations based on the intensity of antibody staining, as well as other parameters such as cell size and light scatter. Although the absolute level of staining may differ with a particular fluorochrome and antibody preparation, the data can be normalized to a control.

The labeled cells are then separated as to the expression of designated marker (e.g., CD4, CD25, etc.). The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Cell populations highly enriched for a desired characteristic (e.g., CD4+ T cells, CD4+CD25+ regulatory T cells, etc.) are achieved in this manner. The desired population will be at or about 70% or more of the cell composition, and usually at or about 90% or more of the cell composition, and may be as much as about 95% or more of the cell population. The enriched cell population may be used immediately. Cells can also be frozen, although it is preferable to freeze cells prior to the separation procedure. Alternatively, cells may be frozen at liquid nitrogen temperatures and stored for long periods of time, being thawed and capable of being reused. The cells will usually be stored in DMSO and/or FCS, in combination with medium, glucose, etc. Once thawed, the cells may be expanded by use of growth factors, antigen, stimulation, antigen presenting cells (e.g., dendritic cells), etc. for proliferation and differentiation.

In some aspects, the present methods are useful for ex vivo generation of regulatory T cells for transplantation into a patient or development of in vitro models and assays for regulatory T cell function. The regulatory T cell cultures serve as a valuable source of novel regulatory factors and pharmaceuticals. Common hypersensitivity therapeutics are used to block the terminal events of tissue damage or target the terminal mediators of the hypersensitivity response (e.g., inflammatory cytokines, IgE, etc.) but generally do not alter the underlying hypersensitivity response. While not wishing to be bound by theory, the strategy of the methods disclosed herein is to produce remission by restoring normal regulatory cell function and thus "resetting" the immune system using regulatory T cells made according to the disclosure herein.

Once the PBMCs or isolated T cells have undergone any necessary pre-treatment, the cells are treated with SAP. By "treated" herein is meant that the cells are incubated in a suitable nutrient medium with SAP for a time period sufficient to produce regulatory T cells having the capacity to inhibit immune responses mediated by effector T cells. In some embodiments, the first culture is diluted with about an equal volume of nutrient medium. In other aspects, a first cell culture is divided into two or more portions that are then diluted with nutrient medium. The advantage of culture division is that the cell clusters formed in the first culture (thousands of cells) are mechanically disrupted and form smaller cell clusters (tens to hundreds of cells) during division of the first culture. These small clusters are then able to grow into larger clusters during the next growth period. A cell culture produced in this fashion may be subcultured two or more times using a similar method. In some embodiments, the second culture or any subsequent culture is substantially free of SAP, for example, the culture may contain less than 10 µg/ml, preferably less than 0.1 µg/ml, or more preferably less than 0.001 µg/ml. A culture that is substantially free of SAP is one in which the concentration of SAP is not sufficient to promote the generation of regulatory T cells.

A cell population may be grown in vitro under various culture conditions. Culture medium may be liquid or semisolid (e.g., containing agar, methylcellulose, etc.), The cell population may be conveniently suspended in any appropriate nutrient medium, including but not limited to Iscove's modified Dulbecco's medium, or RPMI-1640, normally supplemented with fetal calf serum (about 5-10%), L-glutamine, and antibiotics (e.g., penicillin and streptomycin).

The cell culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include the interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, etc.) and antigens (e.g., peptide antigens, protein antigens such as alloantigens) preferably in combination with antigen presenting cells, lectins, non-specific stimuli (e.g., Con A; LPS; etc.). The culture may also contain antibodies (e.g., anti-CD3), or specific ligands (in the form of purified ligand, Fc fusion proteins, or other recombinant tagged forms like leucine zipper forms) for cell surface receptors that may stimulate or inhibit regulatory T cell activity. For example, mAb or ligands that bind TNFR or other co-stimulatory molecules on regulatory T cells and could stimulate and increase regulatory T cell activity, override regulatory T cell activity (and induce proliferation), or that stimulate apoptosis of regulatory T cell can be included. The specific culture conditions are typically chosen to achieve a particular purpose (i.e., maintenance of regulatory T cell activity, expand the regulatory T cell population, etc.). The regulatory T cell may be co-cultured with immature or mature dendritic cells, as well as other antigen presenting cells (e.g., monocytes, B cells, macrophages, etc.) prior to, during, or after treatment with SAP. The regulatory T cells may be co-cultured with other T cell populations. In some aspects, the culture also contain vitamin D3 and/or Dexamethasone, which have been demonstrated to promote the generation of IL-10-producing regulatory CD4+ T cells (Barrat et al. J. Exp. Med. 195(5): 2002, 603-616).

Genes may be introduced into the regulatory T cells prior to culture or transplantation for a variety of purposes (e.g., prevent or reduce susceptibility to infection, replace genes having a loss of function mutation, increase regulatory T cell potency to inhibit Th cells, to make regulatory T cells home to specific regions in vivo, etc.). Alternatively, vectors may be introduced that express antisense mRNA or ribozymes, thereby blocking expression of an undesired gene. Other methods of gene therapy include the introduction of drug resistance genes to enable transplanted cells to have an advantage and be subject to selective pressure, for example the multiple drug resistance gene (MDR), or anti-apoptosis genes, such as bcl-2. Various techniques known in the art may be used to transfect the target cells (e.g., electroporation, calcium precipitated DNA, fusion, transfection, lipofection, etc). The particular manner in which the DNA is introduced is not critical to the practice of the invention provided it does not affect the viability of the cells.

Many vectors useful for transferring exogenous genes into mammalian cells are available. The vectors may be episomal (e.g., plasmids, virus derived vectors such cytomegalovirus, adenovirus, etc.) or may be integrated into the target cell genome, through homologous recombination or random integration (i.e., retrovirus, including lentivirus-derived vectors such MMLV, HIV-1, ALV, etc.)

In some embodiments, regulatory T cells generated by the methods of the disclosure may be transplanted or reintroduced back into the patient. Methods for adoptive transfer of regulatory T cells are well described in the art, for example, see US Patent Applications 2006/0115899, 2005/0196386, 2003/0049696, 2006/0292164, and 2007/0172947 (the contents of which are hereby incorporated by reference). Therefore, a skilled practitioner would easily be able to transplant or reintroduce the regulatory T cells produced by the methods of the present disclosure into a patient in need thereof. Transplanted T cells may originate from a T cell-containing sample obtained from the patient himself or from another donor not receiving treatment. This is generally done as is known in the art and usually comprises injecting, or other methods of introducing, the treated cells back into the patient via intravenous administration. For example, the cells may be placed in a 50 ml Fenwall infusion bag by injection using sterile syringes or other sterile transfer mechanisms. The cells can then be immediately infused via IV administration over a period of time, into a free flow IV line into the patient. In some aspects, additional reagents such as buffers or salts may be added as well.

In some embodiments, regulatory T cells generated by the methods of the disclosure may be used to treat or prevent a hypersensitivity disorder or condition in a patient by administering a therapeutically effective amount of the regulatory T cells to a patient in need thereof. Regulatory T cells of the disclosure can promote regulatory T cell-mediated suppression of hypersensitivity disorders or conditions. In some embodiments, administration of regulatory T cells, generated by the methods of the disclosure, reduces the number of days a patient is afflicted with a hypersensitivity disorder by at least 1, 2, 3, 4, 5, 6, 7, 8, 9, 10, 15, or more days. In some embodiments, administration of regulatory T cells, generated by the methods of the disclosure, inhibits the onset of a hypersensitivity disorder in a patient by at least 1, 2, 3, 4, 5, 6, 7, 8, 9, 10, 15 or more days.

While the methods of the invention can be used to treat patients afflicted with a hypersensitivity disorder, in some embodiments, the methods are also applied to patients who do not have, but are at risk of developing a hypersensitivity response. In patients at risk of developing a hypersensitivity disorder, treatment with regulatory T cells, generated by the methods of the disclosure, can reduce the number of days a patient is afflicted with or inhibit the onset of a hypersensitivity disorder by at least 1, 2, 3, 4, 5, 6, 7, 8, 9, 10, 15, or more days. In some embodiments, treatment with regulatory T cells, generated by the methods of the disclosure, prevents a hypersensitivity disorder in a patient at risk for developing such a disease. In certain aspects of the disclosure, regulatory T cells are administered to a patient before, during, and/or after treatment with a therapy that causes a hypersensitivity response or puts a patient at risk for developing such a disorder. In certain embodiments, the hypersensitivity response is an adverse immune response in a patient that has undergone, or will undergo, an organ or tissue transplant (e.g., graft-vs-host disease).

Another aspect of the disclosure provides methods for treating hypersensitivity-related disorders by conjoint administration of regulatory T cells and at least one additional active agent. In some embodiments, the additional active agent is a therapeutic agent used to treat or prevent a hypersensitivity disease: anti-IgE antibodies, Th1 agonist, Th2 antagonists, short and long term beta-agonists, corticosteroids, cromolyn, xanthines, and allergen-specific immunotherapy. In some embodiments, the active agent may be an inhibitor of mast cells, histamine, prostaglandins, chemokines, Th1 and Th2 mediators, and cysteinyl leukotrienes. Cytokines suitable for conjoint administration may include, but are not limited to IL-2, IL-4, IL-7, IL-10, TGF-β, IL-15 and/or IL-17. In some embodiments the additional active agent may be a cell population other than regulatory T cells. For example, regulatory T cells may be conjointly administered to a patient in need thereof with one or more antigen presenting cell types, such as monocytes or dendritic cells. In some aspects, these antigen presenting cells may be activated monocytes or dendritic cells. In some aspects the antigen presenting cells are activated by exposure to a stimulating antigen and/or SAP agonists. In some embodiments, the additional active agent may be an SAP agonist. In certain aspects, methods for treating hypersensitivity-related disorders comprise the conjoint administration of regulatory T cell, at least one SAP agonist, and one or more additional active agents. The additional active agents may be administered on a periodic basis.

Any treatment method of the disclosure may be repeated as needed or required. For example, the treatment may be done on a periodic basis. The frequency of administering treatment may be determined by one of skill in the art. For example, treatment may be administered once a week for a period of weeks, or multiple times a week for a period of time (e.g., 3-5 times over a two week period). Generally, the amelioration of the hypersensitivity disease symptoms persists for some period of time, preferably at least months. Over time, the patient may experience a relapse of symptoms, at which point the treatments may be repeated.

After transplanting the cells into the patient, the effect of the treatment may be evaluated, if desired. One of skill in the art would recognize there are many methods of evaluating immunological manifestations of a hypersensitivity disease (e.g., quantification of total antibody titers or of specific immunoglobulins, renal function tests, tissue damage evaluation, etc.). Tests of T cells function such as T cell numbers, phenotype, activation state and ability to respond to antigens and/or mitogens also may be done.

The disclosure also provides kits for treating or preventing hypersensitivity-related disorders that comprise one or more SAP agonists. In some embodiments, the kit may include an additional active agent to be administered conjointly with one or more SAP agonists. In some embodiments the additional agent is a therapeutic agent used to treat or prevent a hypersensitivity disease. Active agents of the invention may include, but are not limited to beta-interferons, corticosteroids, non-steroid anti-inflammatory drugs, tumor necrosis blockers, antimalarial drugs, cyclosporines, tumor necrosis alpha inhibitors, immunosuppressants, immunomodulators, cytokines, anti-graft-rejection therapeutics, and antibody therapeutics. Cytokines suitable for conjoint administration may include, but are not limited to IL-2, IL-4, IL-10, TGF-β, IL-15 and/or IL-17. In certain aspects, the additional active agent is a population of regulatory T cells. The agonist(s) and additional active agents may be formulated to be administered conjointly. The active agents of the kit may be administered separately or in a combination formulation. The active agents may be administered simultaneously or at different dosing schedules.

In some embodiments, the invention further provides kits for the practice of the methods of the invention (i.e., the incubation of cells with the SAP to generate regulatory T cells). The kit may have a number of components. In some aspects, the kit may comprise a cell treatment container that is adapted to receive cells from a patient. The patient may be a normal donor or a patient afflicted with a hypersensitivity disorder or other condition. The container should be sterile. In some embodiments, the cell treatment container is used for collection of the cells, for example it is adaptable to be hooked up to a leukopheresis machine using an inlet port. In other embodiments, a separate cell collection container may be used. The kit may also be adapted for use in an automated closed system to purify specific T cell subsets and expand them for transfer back to the patient.

The form and composition of the cell treatment container may vary, as will be appreciated by those in the art. Generally the container may be in a number of different forms, including a flexible bag, similar to an IV bag, or a rigid container similar to a cell culture vessel. It may be configured to allow stirring. Generally, the composition of the container will be any suitable, biologically inert material (e.g., glass or plastic, e.g., polypropylene, polyethylene, etc.) The cell treatment container may have one or more inlet or outlet ports, for the introduction or removal of cells, reagents, regulatory compositions, etc. For example, the container may comprise a sampling port for the removal of a fraction of the cells for analysis prior to reintroduction into the patient. Similarly, the container may comprise an exit port to allow introduction of the cells into the patient; for example, the container may comprise an adapter for attachment to an IV setup.

The kit further comprises at least one dose of a composition comprising a SAP agonist and optionally one or more additional active agent (e.g., cytokines, mitogens, etc.). The components may be used as separate doses or combined. For example, SAP can be combined with at least one or more cytokines and/or one or more mitogens. The kit may also contain at least one dose of a second regulatory composition containing one or more cytokines (e.g., IL-2, IL-7, IL-10, IL-15, IL-17, etc.), mitogens or additional active agents. In some embodiments, the additional active agent may be a therapeutic agent used to treat or prevent a hypersensitivity disease. Active agents of the kit may include, but are not limited to anti-IgE antibodies, Th1 agonist, Th2 antagonists, short and long term beta-agonists, corticosteroids, cromolyn, xanthines, and allergen-specific immunotherapy. In some embodiments, the active agent of the kit may be an inhibitor of mast cells, histamine, prostaglandins, chemokines, Th1 and Th2 mediators, and cysteinyl leukotrienes. Cytokines suitable for administration may include, but are not limited to IL-2, IL-4, IL-10, TGF-β, IL-15 and/or IL-17 hypersensitivity therapeutic.

The kit may also contain at least one dose of nutrient media for diluting the first culture and/or to dissolve lyophilized kit components. "Dose" in this context means an amount of the composition that is sufficient to cause an effect (i.e., SAP agonist induced expansion of regulatory T cells). In some cases, multiple doses may be included. In one embodiment, the dose may be added to the cell treatment container using a port; alternatively, in a preferred embodiment, the first regulatory composition is already present in the cell treatment container. In some embodiments, the regulatory compositions and/or nutrient media are lyophilized for stability, and are reconstituted using nutrient media, or other reagents. In some embodiments, the kit may additionally comprise at least one reagent, including buffers, salts, media, proteins, drugs, etc. For example, mitogens, monoclonal antibodies and treated magnetic beads for cell separation can be included. In some embodiments, the kit may additionally comprise written instructions for using the kits.

Hypersensitivity Related Disorders

Most hypersensitive disorders are characterized as uncontrolled or excessive responses against foreign antigens that results in tissue injury. In some embodiments, the hypersensitivity disorder is systemic or local. Hypersensitivity disorders that may be amenable to treatment with the subject method are Th2-mediated diseases that include, but are not limited to, allergic rhinitis, allergic sinusitis, allergic conjunctivitis, allergic bronchoconstriction, allergic dyspnea, allergic increase in mucus production in the lungs, atopic eczema, dermatitis, urticaria, anaphylaxis, pneumonitis, and allergic-asthma.

In some embodiments, the anti-hypersensitivity therapy composition may be used to treat allergen-specific immune responses, such as anaphylaxis, to various antigens, including, but not limited to, antimicrobials (e.g., cephalosporins, sulfonamides, penicillin and other β-lactams), anticonvulsants (e.g., phenyloin, phenobarital, carbamazepine, dapsone, allopurinal, and minocycline), chemotheraputics (e.g., taxanes, platinum compounds, asparaginases, and epipodophyllotoxins), heparin, insulin, protamine, aspirin and other non-steroidal anti-inflammatory drugs, muscle relaxants (e.g., succinylcholine, atracurium, vecuronium, and pancuronium), induction agents (e.g. barbiturates, etomidate, propofol), narcotics (e.g., fentanyl, meperidine, morphine), colloids for intravascular volume expansion, radiocontrast materials, blood products, latex, animal products, animal dander, dust mites, insects (e.g., bites, stings or venom), cosmetics, metals (e.g., nickel, cobalt, and chromate), plants, spores, pollen, food (e.g., milk, eggs, wheat, soy, peanuts and tree nuts, seafood), vaccination, and fungal antigens (e.g., common allergic species include *Aspergillus, Curvularia, Exserohilum*, and *Alternaria*).

Anti-hypersensitivity therapy compositions may be applied locally or systemically. The compositions may also be supplied in combinations or with cofactors.

Anti-hypersensitivity therapy compositions may be supplied to a target location from an exogenous source, or they may be made in vivo by cells in the target location or cells in the same organism as the target location.

Anti-hypersensitivity therapy compositions may be in any physiologically appropriate formulation. They may be administered to an organism by injection, topically, by inhalation, orally or by any other effective means.

The same compositions and methodologies described above to suppress or inhibit excessive hypersensitivity responses may also be used to suppress or inhibit inappropriate hypersensitivity responses. For example, they may treat, inhibit or reduce a condition occurring in the respiratory system, eye, skin, mouth, gastrointestinal tract, or systemically.

Allergic Asthma

Allergic asthma is an inflammatory disease characterized by reversible airflow limitation and airway hyperresponsiveness. Persistent inflammation in airway tissue may lead to structural changes known as airway remodeling and consequently airway obstruction. The structural changes observed in persistent chronic-asthma, which include airway smooth muscle hypertrophy and hyperplasia, hyperplasia of goblet cells, thickening of airway mucosa and an increase in vascularity, are derived from airway inflammation. Airway inflammation is generally believed to eventually cause tissue injury and subsequent structural changes known as airway remodeling in patients with asthma. One consequence of prolonged inflammation is thickening of the airway wall. In certain embodiments, the anti-hypersensitivity therapy of the present invention may be used to treat allergic-asthma responses in a patient, reducing airway inflammation and thereby preventing airway remodeling.

There are many inflammatory factors produced by airway epithelial cells, and epithelial damage participates in the pro-inflammatory processes through cytokines, growth factors, and mediators in asthma patients. The factors contributing to remodeling directly are transforming growth factor (TGF), platelet-derived growth factor (PDGF), epidermal growth factor (EGF), basic fibroblast growth factor (bFGF), insulin-like growth factor 1 (IGF-1), endothelin-1 (ET-1) and heparin-biding epidermal growth factor (HB-EGF). Airway mucus normally protects the epithelial surface from injury and facilitates the removal of bacterial, cellular, and particulate debris from the lung. Excessive mucus production is also an important feature of allergic- and chronic-asthma and contributes substantially to morbidity and mortality. Goblet cells and submucosal glands secrete mucus, and a high proportion of goblet cells and an enlargement of submucosal glands are associated with hypersecretion of mucus, which may result in the narrowing of airway lumen and therefore, aggravation of airway obstruction.

Studies on models of allergic-asthma implicate the role of Th2 cytokines, particular IL-4, IL-5, IL-9, and IL-13) in goblet cell metaplasia. IL-13 increases the proportion of secretory cells, caused by overexpression of MUC5AC in the same cells, and consequently altered epithelial cell morphology in airway epithelial cells. In addition, IL-13 has been shown to induce goblet cell metaplasia and MUC5AC mucin production in airway epithelium, suggesting that these effects may be attributed to EGFR activation by neutrophils recruited into the airways.

Allergic-asthma patients also have elevated level of STAT-6 in the airway epithelium. Other candidate molecules associated with goblet cell hyperplasia are human $Ca^{2+}$ activated chloride channel-1 (CLCA1) and amphiregulin. Recent studies have demonstrated that the expression of CLCA1 gene is upregulated in goblet cells in patients with allergic-asthma and that amphiregulin, one of the EGFs, produced by stimulation of mast cell FcεRI enhances the expression of mucin mRNA in airway epithelium.

An increase in airway smooth muscle mass is the most prominent feature of airway remodeling in chronic-asthma. Smooth muscle proliferation consists of hypertrophy, the increase in size of airway smooth muscle, and hyperplasia, the increase in the number of airway smooth muscle cells. The increase in smooth muscle mass is disproportionate to the increase in total airway wall thickness. Recent studies suggest that airway smooth muscle cells might modulate airway remodeling by secreting cytokines, growth factors, or matrix proteins and by expressing cell adhesion molecules and other potential costimulatory molecules. Major factors for airway smooth muscle proliferation include EGF, PDGF, TNF-α, tryptase, histamine, and serotonin, and the major inhibitory factors include heparin, β2-agonist, and corticosteroids.

In chronic-asthmatic airways, hyperplasia of airway smooth muscle is an important mechanism leading to increased smooth muscle mass, and it is thought that smooth muscle hyperplasia depends on the stimulation of mitosis and the suppression of apoptosis. There may be at least three major signal transduction pathways associated with airway smooth muscle proliferation: 1) receptor tyrosine kinase (RTK), which is stimulated by PDGF, EGF, bFGF, and IGF, 2) G protein-coupled receptor (GPCR), which is stimulated by thromboxan $A_2$, histamine, ET-1, and $LTD_4$, and 3) cytokine receptor which is stimulated by IL-6 and TNFα.

Several cytokines, especially Th2 cytokines, have a direct role in propagation of the allergic-asthmatic inflammatory processes. IL-13 is critically important in acute models of allergic inflammation, inducing eosinophil-, macrophage-, and lymphocyte-mediated inflammatory responses, subepithelial fibrosis, mucus hypersecretion, and airway hyperresponsiveness. These effects are probably derived from STAT-6 signaling pathway.

Inflammatory Eye Disease

In some embodiments, anti-hypersensitivity compositions of the disclosure may be used to treat, prevent, or reduce the severity of an inflammatory eye disease. (See, e.g., Sugita et al. Invest Opthalmol Vis Sci 2009; Sugita et al. J. Immuno. 183(8): 5013-22, 2009; Gregerson et al. J. Immunol. 183(2) 814-22, 2009; Matta et al. Am J. Pathol. 173(5): 1440-54, 2008; Siemasko et al. Invest Opthalmol Vis Sci. 49(12): 5434-40, 2008; Caspi, R. Immunol Res. 42(1-3): 41-50, 2008; Nanke et al. Mod Rheumatol. 18(4): 354-8, 2008; Agarwal et al. J. Immunol. 180(8): 5423-9, 2008; Ng et al. Invest Opthalmol Vis Sci. 48(11): 5122-7, 2007; and Silver et al. J. Immunol. 179(8): 5146-58, 2007). In particular, anti-hypersensitive compositions of the disclosure may be used to treat, prevent, or reduce the severity of uveitis and/or uveoretinitis. (See, e.g., Commodaro et al. Invest Opthalmol Vis Sci. 2009; Sun et al. Invest Opthalmol Vis Sci. 51(2): 816-21, 2010; Yeh et al. Arch Opthalmol, 127(4): 407-13, 2009; and Ke et al. Invest Ophalmol Vis Sci. 49(9): 3999-4007). For example, compositions of the disclosure may be used to treat granulamatomatous anterior uveitis, resulting from an infection (e.g., HSV, VZV, etc.), cancer, or autoimmune disorder (e.g., Wegener's granulomatosis); nongranulomatous anterior uveitis, particularly in association with keratitis, scleritis, iris atrophy, Arthralgia, or cancer; intermediate uveitis, resulting from infection, cancer, juvenile rheumatoid arthritis, multiple sclerosis, sarcoidosis, pars planitis, vitritis, or peripheral uveitis; posterior uveitis, particularly in association with retinal hemorrhage, neurosensory retinal detachment, focal retinitis, optic disc edema, or retinal vasculitis; or complications resulting from uveitis (e.g., retinal detachment, choroidal detachment, vitreous opacification, glaucoma, calcific band-shaped keratopathy, or cataracts). In certain aspects, the anti-hypersensitive compositions of the disclosure may be used to treat, prevent, or reduce the severity of dry eye diseases including, for example, aqueous tear deficiency (e.g., Sjogrens), evaporative tear production dysfuction (e.g., sarcoid), as well as structural and exogenous disorders (e.g., limpic keratoconjunctivitis). (See, e.g., Chauhan et al. J. Immunol. 182(3): 1247-52, 2009). In certain aspects, the anti-hypersensitive compositions of the disclosure may be used to treat, prevent, or reduce the severity of allergic conjunctivitis disorders. (See, e.g., Sumi et al. Int Arch Allergy Immunol. 148(4): 305-10, 2009; Niederkorn J. Curr Opin Allergy Clin Immunol. 8(5): 472-6, 2008; and Fukushima et al. Allergol Int. 57(3): 241-6, 2008). In certain aspects, anti-hypersensitive compositions of the disclosure may be used to treat, prevent, or reduce the severity of inflammatory eye diseases associated with corneal transplant. (See, e.g., Jin et al. Invest Opthalmol vis Sci. 51(2): 816-21, 2010; and Chauhan et al. J. Immunol. 182(1): 143-53, 2009). In certain aspects, anti-hypersensitive compositions of the disclosure may be used to treat, prevent, or reduce the severity of an inflammatory eye disease associated with a neoplastic disorder. In certain aspects, anti-hypersensitive compositions of the disclosure may be used to treat, prevent, or reduce the severity of an inflammatory eye disease associated with a congenital disorder Anti-hypersensitivity Therapeutics SAP Agonists One aspect of the disclosure provides SAP agonists useful in the treatment of various disorders, in particular, hypersensitivity disorders. SAP agonists encompass all compounds and compositions that increase or otherwise mimic endogenous SAP signaling, including compounds that increase SAP activity.

(i) Human Serum Amyloid P

In certain embodiments, an SAP signaling agonist is an SAP polypeptide or variant thereof. In certain embodiments, an SAP polypeptide is SAP comprising five human SAP protomers (SEQ ID NO: 1). The term "SAP protomer" is intended to refer to a polypeptide that is at least 60%, at least 70%, at least 80%, at least 85%, at least 90%, at least 95%, at least 97%, at least 99% or 100% identical to human SAP protomer, as determined using the FASTDB computer program based on the algorithm of Brutlag et al. (*Comp. App. Biosci.,* 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05. The term "SAP protomer" encompasses functional fragments and fusion proteins comprising any of the preceding. Generally, an SAP protomer will be designed to be soluble in aqueous solutions at biologically relevant temperatures, pH levels and osmolarity. The protomers that non-covalently associate together to form SAP may have identical amino acid sequences and/or post-translational modifications or, alternatively, individual protomers may have different sequences and/or modifications.

Some aspects of the invention provide polypeptides, or provide therapeutic methods for employing those polypeptides, wherein said polypeptides are defined, at least in part, to a reference sequence. Accordingly, such polypeptides may have a certain percentage of amino acid residues which are not identical to a reference sequence. In some embodiments, the non-identical residues have similar chemical properties to the residues to which they are not identical. Groups that have similar properties include the following amino acids: E, D, N, and Q; H, K, and R; Y, F and W; I, L, V, M, C, and A; and S, T, C, P, and A.

In some embodiments, the residues that are not identical are those that are not evolutionarily conserved between the reference sequence and an orthologous sequence in at least one evolutionarily related species, such as in species within the same order. In the case of a vertebrate reference sequence, the amino acids that may be mutated in a preferred embodiment are those that are not conserved between the reference sequence and the orthologous sequence in another vertebrate species. For example, if a polypeptide used in a method of the present invention is said to comprise an amino acid sequence that is at least 95% identical to human SAP (SEQ ID NO:1), then said polypeptide may have non-identical residues to those positions in which the human SAP and that of another vertebrate differ. FIG. 1 depicts human SAP aligned against two mammalian and one avian SAP sequence. Unshaded residues indicate residues that differ from the human SAP sequence.

Polypeptides sharing at least 95% identity with SEQ ID NO:1 include polypeptides having conservative substitutions in these areas of divergence. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent can be found in Bowie et al., Science 247:1306-1310 (1990).

SAP polypeptides typically comprise polymers that are at least 60%, at least 70%, at least 80%, at least 85%, at least 90%, at least 95%, at least 97%, or at least 99% identical to SEQ ID NO. 1.

In some embodiments, pharmaceutical compositions are provided comprising SAP, or a functional fragment thereof. In some embodiments, pharmaceutical compositions are provided comprising an SAP variant. The amino acid sequence of a SAP variant may differ from SEQ ID NO: 1 by one or more conservative substitutions. As used herein, "conservative substitutions" are residues that are physically or functionally similar to the corresponding reference residues, i.e., a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. Additional guidance concerning which amino acid changes are likely to be phenotypically silent can be found in Bowie et al., Science 247:1306-1310 (1990).

Variants and fragments of SAP that retain biological function are useful in the pharmaceutical compositions and methods described herein. In some embodiments, a variant or fragment of SAP binds FcγRI, FcγRIIA, and/or FcγRIIIB In some embodiments, a variant or fragment of SAP is used to treat or prevent and autoimmune disorder or condition.

In specific embodiments of the present invention, compositions containing SAP, SAP variants, or SAP functional fragments may be operable to raise SAP concentration in target locations to approximately at least 0.5 µg/ml. A functional fragment of SAP is a portion of the SAP polypeptide that retains native SAP activity. In humans, $^{125}$I radio-labeled SAP has been previously administered to study patients with amyloidosis. In the treatments, approximately 600 µg of SAP was administered to an adult human. Accordingly, administration of approximately 600 µg of SAP systemically to an adult human is safe. Higher dosages may also be safe under appropriate conditions.

(ii) Anti-FcγR Antibodies as SAP Agonists

In one aspect of the invention, one or more compounds are provided that mimic SAP signaling. In some embodiments, the SAP signaling agonists are anti-FcγR antibodies, wherein the antibodies are selected from a class of anti-FcγRI, anti-FcγRIIA, and anti-FcγRIII antibodies that are able to bind to either FcγRI, FcγRIIA, or FcγRIII, respectively. Anti-FcγR antibodies are IgG antibodies that bind to receptors for the Fc portion of IgG antibodies (FcγR). The anti-FcγR antibodies bind through their variable region, and not through their constant (Fc) region. Anti-FcγR antibodies may include any isotype of antibody. The anti-FcγR antibodies may be further cross-linked or aggregated with or without additional antibodies or other means. This process initiates intracellular signaling events consistent with FcγR activation. In some embodiments, the SAP signaling agonist may be a cross-linked FcγR.

Compositions containing anti-FcγRI antibodies, anti-FcγRII antibodies, and/or anti-FcγRIII antibodies may be used to suppress hypersensitive disorders in inappropriate locations.

In specific embodiments, compositions containing approximately 1.0 µg/mL anti-FcγR antibodies may be effective to inhibit hypersensitive disorders by approximately 50%. In other embodiments, compositions may contain an amount sufficient to deliver 1.0 µg/mL anti-FcγR antibodies to the target tissue.

Anti-FcγR antibodies may be administered in a dose of approximately 1.0 µg/mL, in an amount sufficient to deliver 1.0 µg/mL anti-FcγR antibodies to the target tissue, or in another dose sufficient to inhibit hypersensitive disorders without causing an undesirable amount of cell death in the patient.

(iii) Aggregated Fc Domains and Fc-containing Antibodies

In some embodiments, the SAP signaling agonists are cross-linked or aggregated IgG. Cross-linked or aggregated IgG may include any IgG able to bind the target FcγR through its Fc region, provided that at least two such IgG antibodies are physically connected to one another.

Cross-linked or aggregated IgG may include whole antibodies or a portion thereof, preferably the portion functional in suppression of hypersensitive disorders. For example, they may include any antibody portion able to cross-link FcγR. This may include aggregated or cross-linked antibodies or fragments thereof, such as aggregated or cross-linked whole antibodies, F(ab')$_2$ fragments, and possible even Fc fragments.

Aggregation or cross-linking of antibodies may be accomplished by any known method, such as heat or chemical aggregation. Any level of aggregation or cross-linking may be sufficient, although increased aggregation may result in increased hypersensitive disorder suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

Compositions containing cross-linked or aggregated IgG may be used to suppress the hypersensitive disorders in inappropriate locations.

In other specific embodiments, compositions may contain as little as 0.1 µg ml cross-linked or aggregated IgG. Aggregated or cross-linked IgG may be administered in an amount sufficient to deliver at least 0.1 µg/ml/gG to the target tissue, or in another dose sufficient to inhibit hypersensitive disorders without causing an undesirable amount of cell death in the patient.

(iv) SAP Peptidomimetic

In certain embodiments, the SAP agonists include peptidomimetics. As used herein, the term "peptidomimetic" includes chemically modified peptides and peptide-like molecules that contain non-naturally occurring amino acids, peptoids, and the like. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of SAP polypeptides.

(v) Increase SAP Activity

In some embodiments, an SAP agonist increases SAP activity. SAP activity can be increased by increasing the concentration of SAP by, for example, increasing SAP transcription, increasing translation, increasing SAP secretion, increasing SAP RNA stability, increasing SAP protein stability, or decreasing SAP protein degradation. SAP activity can also be increased by increasing specifically the "free concentration" of SAP, or rather the unbound form by, for example, decreasing SAP endogenous binding partners.

(iv) FcγR Crosslinkers

In some embodiments, fibronectin based scaffold domain proteins may be used as SAP agonists to crosslink FcγRs. Fibronectin based scaffold domain proteins may comprise a fibronectin type III domain (Fn3), in particular a fibronectin type III tenth domain ($^{10}$Fn3).

In order to crosslink FcγRs, multimers of FcγR binding Fn3 domains may be generated as described in U.S. Pat. No. 7,115,396.

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. The BC, DE, and FG loops are both structurally and functionally analogous to the complementarity-determining regions (CDRs) from immunoglobulins Fn3 domains can be designed to bind almost any compound by altering the sequence of one or more of the BC, DE, and FG loops. Methods for generating specific binders have been described in U.S. Pat. No. 7,115,396, disclosing high affinity TNFα binders, and U.S. Publication No. 2007/0148126, disclosing high affinity VEGFR2 binders. An example of fibronectin-based scaffold proteins are Adnectins™ (Adnexus, a Bristol-Myers Squibb R&D Company).

In some embodiments, the SAP agonist is an aptamer. In order to crosslink FcγRs, multimers of FcγR binding aptamers may be generated.

Aptamers are oligonucleotides, which can be synthetic or natural, that bind to a particular target molecule, such as a protein or metabolite. Typically, the binding is through interactions other than classic Watson-Crick base pairing. Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In vitro Cell. Dev. Biol. Anim 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. Systematic Evolution of Ligands by Exponential Enrichment, "SELEX™," is a method for making a nucleic acid ligand for any desired target, as described, e.g., in U.S. Pat. Nos. 5,475, 096 and 5,270,163, and PCT/US91/04078, each of which is specifically incorporated herein by reference.

In some embodiments, SAP agonists are Nanobodies®. Nanobodies® are antibody-derived therapeutic proteins that contain the unique structural and functional properties of naturally-occurring heavy-chain antibodies. The Nanobody® technology was originally developed following the discovery that camelidae (camels and llamas) possess fully functional antibodies that lack light chains. These heavy-chain antibodies contain a single variable domain (VHH) and two constant domains (CH2 and CH3). Importantly, the cloned and isolated VHH domain is a stable polypeptide harbouring the full antigen-binding capacity of the original heavy-chain antibody. These newly VHH domains with their unique structural and functional properties form the basis of a new generation of therapeutic antibodies.

Pro-Hypersensitivity Factor Antagonists

Anti-hypersensitivity therapy encompasses agents that inhibit or antagonize pro-hypersensitivity factors, such as agents that antagonize one or more growth factors or cytokines involved in the formation and maintenance of a hypersensitivity response. In this manner, anti-hypersensitivity therapy may be used to antagonize the activities of cells involved in hypersensitivity responses including Th2 T-cells, mast cells, basophils, B-cells (plasma), eosinophils, macrophages, dendritic cells.

Pro-hypersensitivity factors that may be targets with antagonists as part of the therapies of the present invention include, without limitation, IL-4, IL-13, IL-5, IL-9, IL-15, IL-17A, IL-17E, IL-33, IL-21, TSLP, IgE, histamine, allergic prostaglandins, and cysteinyl leukotrienes and other factors known to promote or be related to maintenance of hypersensitivity disorders.

In certain embodiments, anti-hypersensitivity therapy may include antibodies directed to one or more of the pro-hypersensitivity factors. Such antibodies may be purified, unpurified, or partially purified. The antibodies may be polyclonal or monoclonal antibodies, derived from any suitable animal source, such as mouse, rabbit, rat, human, horse, goat, bovine, and the like. Such antibodies may include antibody fragments, single chain antibodies, polymerized antibodies and/or antibody fragments and the like.

In certain embodiments, anti-hypersensitive therapy may include antagonists of the corresponding receptor of one or more of the pro-hypersensitivity factors and/or cytokines, such as fragments thereof. Such forms in suitable concentration may compete with its corresponding pro-hypersensitivity factors and/or cytokines for binding to its receptor. Similarly, certain antibodies to the receptor may be used to interfere with or prevent binding thereto of the corresponding pro-hypersensitivity factors and/or cytokines.

In other selected embodiments, anti-hypersensitivity therapy may include soluble forms of the receptor of one or more of the pro-hypersensitivity factors and/or cytokines, such that the soluble receptor competes with its corresponding native cellular receptor for that ligand.

In other selected embodiments, anti-hypersensitivity therapy may include compounds that compete with or otherwise interfere with binding of one or more of the pro-hypersensitivity factors and/or cytokines with its receptor.

In certain embodiments, anti-hypersensitivity therapy may include one or more oligoribonucleotides that contain at least one sequence that is antisense with respect to one or more of the pro-hypersensitivity factors and/or cytokines. Such components may also include one or more expression plasmids having suitable transcriptional control sequences that yield antisense sequences. In other selected embodiments, anti-hypersensitivity therapy may include one or more double-stranded oligoribonucleotides, or expression plasmids encoding thereof, that are suitable for degrading transcripts of one or more of the pro-hypersensitivity factors and/or cytokines via RNA-mediated interference. In other selected embodiments, anti-hypersensitivity therapy may include one or more single-stranded oligonucleotide aptamers, or expression plasmids encoding thereof, that are suitable for inhibiting the binding of pro-hypersensitivity factors to their cognate receptors.

A suitable pro-hypersensitivity factor antagonist may include components known to inhibit, attenuate, or interfere with one or more components of the intracellular signaling pathways activated by one or more of the pro-hypersensitivity factors upon binding to its corresponding receptor. For example, the transcription factor STATE in naive CD4+ T-cells is activated by IL-4 and stimulates Th2 development. Similarly, GATA-3, another transcription factor, produced in response to antigen recognition and enhanced by IL-4 to amplify the mechanisms of Th2 responses. Both of these transcriptional regulators are important for the development of the Th2 cells and therefore are responsible for promoting hypersensitivity responses.

In other selected embodiments, a suitable anti-hypersensitivity factor antagonist may include inhibitors of histamine, prostaglandin, and cysteinyl leukotriene precursors.

Corticosteroids

Th2-cell-mediated inflammation, particularly in allergic-asthmatic airways, is suppressed by corticosteroids through the inhibition of expression of cytokines, chemokines, and adhesion molecules, whose encoding genes are regulated by transcription factors such as nuclear factor-κB (NF-κB) and activation protein 1 (AP1).

β2-adrenoceptor Agonists

Short- and long-acting β2-adrenoceptor agonists (SABAs and LABAs) are one of the most effective treatments for rapid relief of allergic responses. In particular, inhaled SABAs, like salbutamol and terbutaline, are the most effective bronchodilators currently available for the rapid relief of allergic-asthma symptoms. After binding of these agonists to the β2-adrenoceptor, adenylate cyclase is stimulated by the signal-transduction of G protein to increase production of cyclic adenosine 3'5'-monophosphate (cAMP), thereby activating protein kinase A. This mediates smooth muscle relaxation through the phosphorylation of myosin light-chain kinase and by opening $Ca^{2+}$-dependent $K^+$ (KCa) channels, which relieves bronchoconstriction in allergic-asthma. Two inhaled LABAs, formoterol and salmeterol, induce bronchodilation for at least 12 hours and are used as a supplementary therapy for allergic-asthma that is not controlled by inhaled corticosteroids. LABAs may increase the efficacy of inhaled corticosteroids.

Cromoglicate

Cromoglicate (also referred to as cromolyn or cromoglycate) is traditionally described as a mast cell stabilizer, and is commonly marketed as the sodium salt sodium cromoglicate or cromolyn sodium. This drug prevents the release of inflammatory chemicals such as histamine from mast cells. It is available as a nasal spray (Rynacrom, Nasalcrom, Prevalin) to treat allergic rhinitis, as an inhaler (Intal) for preventive management of allergic-asthma, as eye drops (Opticrom and Optrex Allergy, Crolom) for allergic conjunctivitis, or in an oral form (Gastrocrom) to treat mastocytosis, dermatographic urticaria and ulcerative colitis. Sodium cromoglicate has also been shown to reduce symptoms of food allergies.

Xanthines

Xanthine is a purine base found in most body tissues and fluids. Derivatives of xanthine, known collectively as xanthines, are a group of alkaloids commonly used for their effects as mild stimulants and bronchodialtors, notably in treating the symptoms of allergic-asthma. Due to undesired, systemic side-effects, the therapeutic range of xanthines is narrow, making them a second-line allergic-asthma treatment. The therapeutic level is 10-20 µg/mL in blood.

Effector Antagonists and Inhibitors

Anti-H1-histamines, such as chlorphenitamine, were first used as specific agents to treat allergic reactions. A second generation of drugs includes cetirizine, levocetirizine, loratadine, and desloratadine.

The CysLts are the most potent contractile agonists of airway smooth muscle and they also have effects on microvessel, mucous glands, eosinophils and nerves by interacting with the CysLT receptor 1 (CysLTR1) during active allergic-asthma and rhinitis; increased levels of $CysLTC_4$, $CysLTD_4$, and $CysLTE_4$ have been detected in biological fluids. Neither the biosynthesis nor the actions of CysLTs are inhibited by corticosteroids. The currently available oral leukotriene modifiers are CysLTR1 antagonists (montelukast, zafirlukast, and pranlukast). Leukotriene inhibitors are also effective for the treatment of allergic rhinoconjunctivitis, but not for the treatment of atopic dermatitis.

Theophyline is a xanthine with activity as both a cAMP phosphodiesterase inhibitor and an adenosine-receptor antagonist. Theophylline has been used to treat allergic-asthmatic bronchoconstriction. Previously, the most effective phosphodiesterase inhibition was achieved by targeting the type-4 isoenzyme with non-xanthine drugs such as rofumulast. Other antagonists include PDE4 and p38 MAP kinase inhibitors.

Treatment of Refractory Disease

There are some patients with hypersensitivity disorders, particularly allergic-asthma, whose symptoms are not adequately controlled by conventional treatments. Calcinerurin inhibitors such as oral cyclosporine A and locally applied tacrolimus and pimecrolimus, are effective treatments for atopic dermatitis that is refractory to corticosteroid treatment. The failure of corticosteroids to decrease the level of expression of TNF and other Th2-cell-associated cytokines in allergic-asthmatic airways might explain why corticosteroids have limited effects in more severe forms of the disease. Based on the increased expression of TNF in the airways and in blood mononuclear cells in severe allergic-asthma, patients may be treated with the soluble TNF-receptor fusion proteins and TNF-specific monoclonal antibodies. Inhibitors of p38 mitogen-activated protein kinase and IκB kinase, such as SB 220025 and TPCA-1, are new therapeutics approaches for refractory allergic-asthma. These drugs inhibit the production of pro-inflammatory cytokines such as TNF and IL-1.

Allergen-specific Immunotherapy

Allergen-specific immunotherapy (SIT) is an immune-modifying therapy that has been recommended for the treatment of allergic rhinitis, venom hypersensitivity, some drug allergies and mild bronchial allergic-asthma. SIT induces immunological tolerance and the induction of blocking IgG4 antibodies through repeated exposure to allergens. After experimental or natural exposure to allergens, SIT decreases the recruitment of mast cells, basophils and eosinophils in the skin, nose, eyes, and bronchial mucosa. SIT produces an increase in the level of allergen-specific IgA and IgG4 antibodies, and a decrease in the level of allergen-specific IgE antibodies. It also induces $CD4^+CD25^+FoxP3^+T_{Reg}$ cells that produce high levels of IL-10 and/or TGFβ, two cytokines that are known to attenuate allergen-specific Th2-cells responses. IL-10 suppresses mast cell, eosinophil and T-cell responses, and the pleiotropic functions of TGFβ maintain a diverse and self-tolerant T-cell repertoire including $T_{Reg}$ cells. Subcutaneous immunotherapy (SCIT) involves the regular subcutaneous injection of allergen extracts or recombinant allergens using incremental regimes, with the induction of tolerance taking from several days to several months depending on the regime used. Once tolerance is induced, it can last for several years without further treatment. Attaching CpG oligonucleotide motifs to purified allergens is a promising approach to SCIT by increasing the efficacy and decreasing the side effects. The administration of allergens to the oral mucosa as a route for immunotherapy has only recently gained acceptance (SLIT). SCIT and SLIT also decrease the development of sensitization to new allergens and decrease the risk of new allergic-asthma in both adults and children with rhinitis.

IgE Antagonism

The sentinel role of IgE is to increase allergen uptake by DCs and activation of mast cells and basophils for mediator release. IgG antibodies specific for the C3 domain of IgE that block IgE binding to FcεRI and FcεRII are known to block allergen-induced inflammatory responses. Omalizumab, a humanized IgE-specific, non-anaphylactic IgG1 has been developed for the treatment of severe allergic-asthma. Omalizumab is also effective for the treatment of allergic rhinoconjunctivitis. Lumiliximab, an antibody specific for the low-affinity IgE receptor FcεRII, also decrease circulating IgE levels and has passed Phase I trials for mild to moderate allergic-asthma.

Mast Cell Inhibitors

The mast-cell-stabilizing drug sodium cromoglicate (SCG) and nedocromil sodium were first introduced as treatments for allergic-asthma. After inhalation, both drugs inhibit the allergen-induced early- and late-phase responses in the upper and lower airways and conjunctiva, where mucosal mast cells are crucially involved in the allergic response. Nedocromil sodium and SCG inhibit the flux of chloride ions in mast cells, epithelial cells and neurons to increase their threshold for activation. Mast cells also express a $Ca^{2+}$-activatied $K^+$ channel, K(CA)3.1, that promotes mast cell chemotaxis and increases IgE-dependent mast cell activation, which indicates that the inhibition of K(Ca)3.1 with drugs such as clotriazol and TRAM-34 would promote mast-cell inhibition.

The SRC tyrosine kinases FYN and LYN are important modulators of the molecular events that are initiated by engagement of FcεRI. They in turn phosphorylate FcεRI associated g-signaling chain which recruits the SYK tyrosine kinase. SYK is then activated through phosphorylation by FYN and LYN. Several treatment methods are directed at inactivating SYK and thereby blocking propagation of FcεRI signaling. R122 (2,4-diaminopyrimidine) has been identified as a reversible mast cell SYK inhibitor. In allergic rhinitis, intranasal administration of R112 inhibits nasal obstruction, rhinorrhoea, and inhibition of prostaglandin $D_2$ production. In patients with seasonal rhinitis, R122 is effective in reducing global symptoms of rhinitis with rapid onset.

The interaction of stem-cell factor (SCF) with its tyrosine-kinase receptor (KIT) is obligatory for mast cell development, proliferation, survival, homing and adhesion, and for optimal IgE-induced mast-cell degranulation and cytokine production. Drug candidates that target SCF or KIT include SCF-specific antibodies, antisense oligonucleotides, KIT inhibitors and inhibitors of downstream signaling molecules. Imatinib mesylate, nilotinib and desatinib are tyrosine-kinase that can induce apoptosis of mast cells.

Modulating the expression of activating and inhibiting receptors is an important mechanism for regulating immune responses. Cells that are activated through ligation of receptors bearing immunoreceptor tyrosine-based activation motifs (ITAMs) can be negatively regulated by other receptors bearing immunoreceptor tyrosine-based inhibitory motifs (ITIMs). Animals deficient in FcγRIIB, gp49B1, or pared immunoglobulin-like receptor B have increased allergic responses. IgG can completely suppress IgE-mediated anaphylaxis by interacting with FcγRIIB, which leads to activation of the SRC homolog 2 (SH2)-domain-containing inositol polyphosphate 5'-phosphatase (SHIP) through recruitment of DOK and RasGAP to FcεRI. Similar inhibitory mechanisms are invoked when ngp49B1 on mast cells is activated by its integrin ligand αvβ3. The immunoglobulin-like receptors and their intracellular signaling molecules provide important therapeutic targets to inhibit mast cells, as well as T cells, involved in the allergic cascade. A human bifunctional Fcγ-Fcε fusion protein designed to crosslink FcγRIIB and FcεRI on human mast cells and basophils inhibits IgE-dependent degranulation and allergic reactions.

Cytokine Immunotherapies

As Th2 cytokines have a major role in orchestrating allergic inflammation, they and their receptors are key therapeutic targets. This approach has required the application of biological agents in the form of blocking monoclonal antibodies, function proteins, and inhibitors of Th2 transcription factors STAT-6 and GATA-3.

A.) IL-4

Both IL-4 and IL-13 have a crucial role in the immunoglobulin isotype switching of B cells to produce IgE, whereas IL-4 alone is responsible for maintaining the Th2-cell phenotype, which makes both cytokines attractive therapeutic targets. Many studies have shown that blocking production of IL-4 has profound effects on the allergic phenotype. A soluble, recombinant, human IL-4 receptor (altrakincept) consists of the extracellular portion of human IL-4Rα and is non-immunogenic. It has been used to treat mild to moderate allergic-asthma and indicated efficacy by allowing withdrawal from treatment with inhaled corticosteroids without relapse. Other studies are in progress using humanized IL-4-specific and IL-4Rα-blocking antibodies such as pascolizumab. Also, two vaccines against IL-4 have been tested and both induced high antibody titers specific for IL-4 and inhibited antigen-inducing lung inflammation.

B.) IL-13

The numerous functions of IL-13 in regulating IgE production, eosinophilic inflammation, airway-smooth-muscle hyperplasia, the induction of goblet-cell hyperplasia with mucus production, and the recruitment of monocytes, macrophages and T-cells into the airway spaces make it a key therapeutic target in allergy and allergic-asthma. IL-13 binds to a low-affinity IL-13Rα1 subunit and a high-affinity complex comprised of IL-13Rα1 and IL-4Rα. Binding to this high affinity complex leads to the phosphorylation-dependent activation of Janus kinase 1 (JAK1), JAK2, and STAT-6. IL-4Rα also stabilizes the binding of IL-13 to its receptor to augment IL-13-mediated responses. However, a non-signaling, high-affinity IL-13-binding chain, IL-13Rα2, strongly inhibits the activity of IL-13. Selective blockade of IL-13 has been achieved using a soluble form of IL-13Rα2, which competes for binding to IL-13 but not to IL-4, and this led to reversal of airway hyperresponsiveness and mucus production in allergen-exposed sensitized animals.

Antagonizing the effects of IL-13 could also be achieved by administering soluble IL-13 receptors of IL-13R-specific monoclonal antibodies. Phase I trails of the IL-13-specific monoclonal antibody CAT-354 has been used to successfully treat mildly allergic-asthmatic patients. Subcutaneous or inhaled pitrakinra, a mutant IL-4 protein that inhibits binding of IL-4 and IL-13 to IL-4Rα complexes, has shown efficacy in the treatment of allergen-induced allergic-asthma. A novel recombinant IL-13 peptide based vaccine has also been shown to reduce allergic inflammatory responses. As STAT-6 is the common transcription factor for both IL-4 and IL-13 signaling, it is also an attractive therapeutic target using a dominant-negative peptide. Anti-sense and RNA interference-based therapeutics strategies could be used to target various upstream signaling molecules in allergic-asthma and allergy, including FcεRIα, cytokine receptors, adhesion molecules, ion channels, cytokine and related factors, intracellular signal-transduction molecules and transcription factors involved in Th2-cell differentiation and allergic inflammation.

C.) IL-5

Rodent and non-human primate studies indicated and important role for IL-5 in various models of allergic-asthma. Inhaled IL-5 modulates the number of eosinophils progenitors in both the airway and bone marrow of allergic-asthmatic individuals and induces local eosinophilia in non-asthmatic individuals. Two humanized, IL-5-specific monoclonal antibodies, Sch-55,700 and mepolizumab, have been developed for the treatment of allergic-asthma. Mepolizumab produces a rapid dose-dependent reduction in the number of circulating and sputum eosinophils. Patients with severe and persistent allergic-asthma treated with Sch-55,700 show a decrease in number of blood eosinophils.

D.) IL-9

Blocking the actions of IL-9 reduces allergen-induced airway inflammation and airway hyperresponsiveness. IL-9-specific monoclonal antibodies are being used to treat patients with moderate to severe, persistent allergic-asthma.

E.) IL-12

IL-12 sends a strong signal to naive precursor T-cells, directing their differentiation to Th1 cells and shifting the immune response towards cell-mediated immunity. Administration of IL-12 during sensitization suppresses allergen-induced Th2-cell responses in factor of Th1-cell development and inhibits airway hyperresponsiveness and airway eosinophilia after antigen challenge. Injection of recombinant IL-12 in patients with mild allergic-asthma decreased the number of circulating blood eosinophils after allergen challenge.

F.) IL-10

IL-10 inhibits the expression of many pro-inflammatory cytokines and chemokines, as well as pro-inflammatory enzymes, and it is the main inhibitory cytokine produced by $T_{Reg}$ cells in allergen immunotherapy. Administration of IL-10 decreases the numbers of circulating CD4+ and CD8+ T cells, with suppression of mitogen-induced T-cell proliferation and endotoxin-driven TNF and IL-1β production.

G.) Interferons

Of the Th1-cell associated cytokines, IFNγ is the most potent in suppressing Th2-cell-mediated allergic inflammation, and the exogenous administration of IFNγ suppresses allergic airway inflammation in animal models. IFNγ is also strongly induced during allergen-specific immunotherapy. Systemic administration of IFNγ is effective for the treatment of severe corticosteroid-refractory allergic-asthma.

Pharmaceutical Preparations and Formulations

In some embodiments, the present invention provides a pharmaceutical composition comprising a regulatory T cell population in a formulation that is suitable for administration to a patient in need thereof. The T cell population for use in the composition may be generated by the methods described herein. In some embodiments, at least 70, 80, 90, or 100% of the cells of the composition are regulatory T cells.

In some embodiments, the pharmaceutical compositions comprise an enriched regulatory T cell population in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. In some embodiments, the pharmaceutical compositions are suitable for treating or preventing an hypersensitivity disorder in a human subject.

In some embodiments, the composition of the present invention contains a therapeutically effective amount of regulatory T cells in combination with an effective amount of one or more active agents. In certain aspects, the active agent comprises at least one cytokine (e.g., IL-2, IL-4, IL-10, TGF-β, and/or IL-15). In certain aspects, the active agent is one or more SAP agonists. In certain embodiments, the additional active agent is a therapeutic agent used to treat hypersensitivity disorders of conditions.

The pharmaceutical composition comprising regulatory T cells is administered to a subject in need thereof in a manner appropriate to the disease to be treated and/or prevented. The dosage and frequency of administration will be determined by such factors as the condition of the patient and the type and/or severity of the patient's disease. Appropriate dosages may also be determined by clinical trials. An "effective amount" of the composition can be determined by a physician with consideration of individual differences in age, weight, disease severity, condition of the patient, route of administration and any other factors relevant to treatment of the patient. In general, a pharmaceutical composition comprising T regulatory cells may be administered at a dosage of about $10^4$ to $10^9$ cells/kg body weight, including all integer values within these ranges. The compositions of the invention may also be administered multiple times at these dosages. The optimal dosage and treatment regime for a particular patient can readily be determined by one skilled in the art of medicine by monitoring the patient for signs of disease and adjusting the treatment accordingly.

The cells can be administered by using infusion techniques that are commonly used in immunotherapy, and may be administered to a patient subcutaneously, intradermally, intramuscularly, or by intravenous injection (see, e.g., Rosenburg et al., New Eng. J. Med.). Compositions of the present invention are preferably formulated for intravenous administration.

In certain embodiments, the methods described herein involve administration of an anti-hypersensitivity therapy to a subject. The therapeutic agents may be formulated in a conventional manner using one or more physiologically acceptable carriers or excipients. For example, therapeutic agents and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some embodiments, the therapeutic agents can be administered to cells by a variety of methods know to those familiar in the art, including, but not restricted to, encapsulation in liposomes, by iontophoresis, or by incorporation into other vehicles, such as hydrogels, cyclodextrins, biodegradable nanocapsules, and bioadhesive microspheres.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

In the methods of the invention, the pharmaceutical compounds can also be administered by intranasal or intrabronchial routes including insufflation, powders, and aerosol formulations (for examples of steroid inhalants, see Rohatagi (1995) J. Clin. Pharmacol. 35:1187-1193; Tjwa (1995) Ann Allergy Asthma Immunol. 75:107-111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer Typically, such administration is in an aqueous pharmacologically acceptable buffer.

Therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, therapeutic agents may also be formulated as a depot preparation. Such long acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, therapeutic agents are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more therapeutic agents described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. Therapeutic agents may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, conjunctiva, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen free environment according to methods in the art.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

Antisense nucleotides, such as siRNA, may be delivered to cancer cells using a variety of methods. Cell-penetrating peptides (CPPs) having the ability to convey linked "cargo" molecules into the cytosol may be used (see Juliano, Ann N Y Acad. Sci. 2006 October; 1082:18-26). In certain embodiments, an atelocollagen-mediated oligonucleotide delivery system is used (Hanai et la. Ann N Y Acad. Sci. 2006 October; 1082:9-17). An LPD formulation (liposome-polycation-DNA complex) may be used to deliver siRNA to tumor cells. (Li et al. Ann N Y Acad. Sci. 2006 October; 1082:1-8). Complexation of siRNAs with the polyethylenimine (PEI) may also be used to deliver siRNA into cells (Aigner, J Biomed Biotechnol. 2006; 2006(4):71659). siRNA may also be complexed with chitosan-coated polyisohexylcyanoacrylate (PIHCA) nanoparticles for in vivo delivery. (Pille et al., Hum Gene Ther. 2006 October; 17(10):1019.

The present invention further provides use of any agent identified by the present invention in the manufacture of a medicament for the treatment or prevention of a hypersensitivity disorder or a condition in a patient, for example, the use of an SAP agonist in the manufacture of medicament for the treatment of a hypersensitivity disorder or condition. In some aspects, any agent identified by the present invention may be used to make a pharmaceutical preparation for the use in treating or preventing a hypersensitivity disease or condition.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXEMPLIFICATION

Example 1

Chronic allergic airway disease induced by *A. fumigatus* conidia is characterized by airway hyper-reactivity, lung inflammation, eosinophilia, mucus hypersecretion, goblet cell hyperplasia, and subepithelial fibrosis. C57BL/6 mice were similarly sensitized to a commercially available preparation of soluble *A. fumigatus* antigens as previously described (Hogaboam et al. The American Journal of Pathology. 2000; 156: 723-732). Seven days after the third intranasal challenge, each mouse received $5.0 \times 10^6$ *A. fumigatus* conidia suspended in 30 µl of PBS tween 80 (0.1%, vol/vol) via intratracheal route.

Figure 2B:
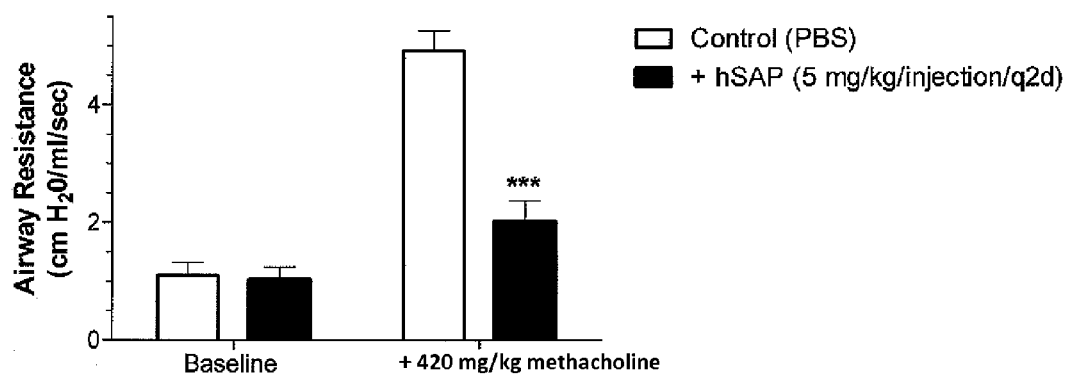
Figure 3A:
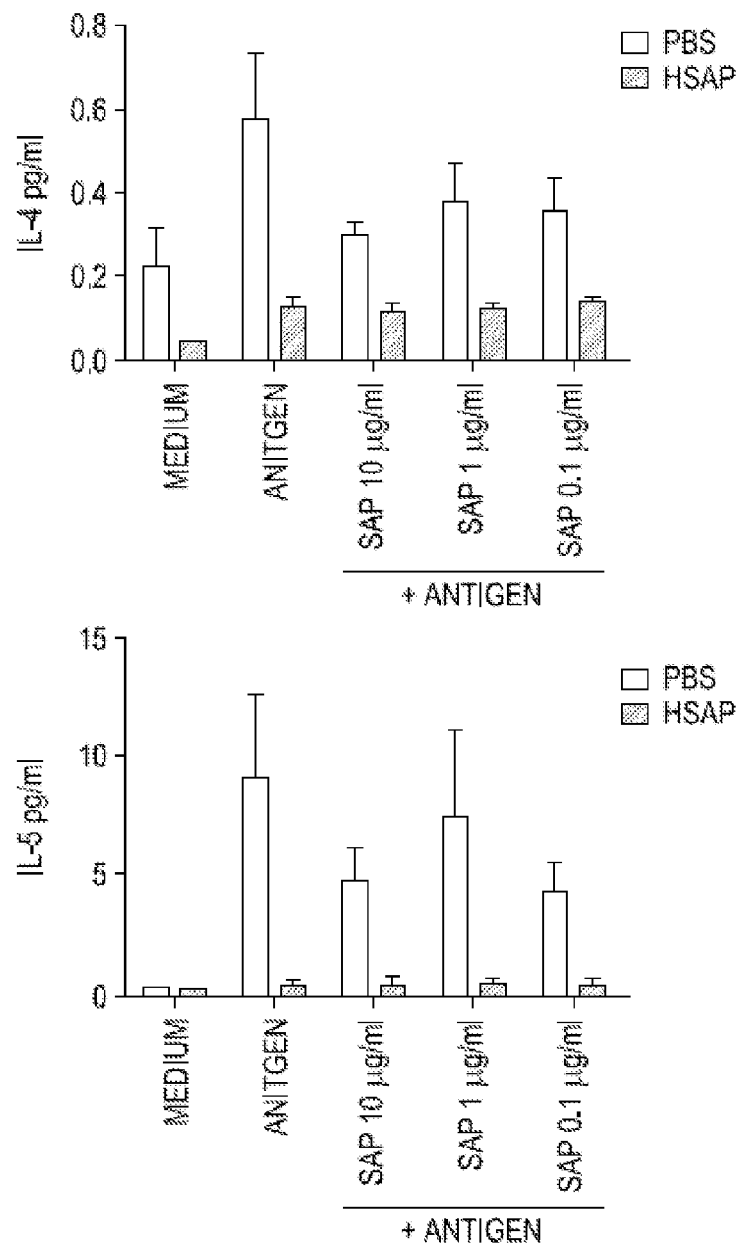
FIGS. 3A-D. Cytokine generation in splenocyte culture from cells isolated and simulated with *aspergillus* antigen and treated in vitro and in vivo with hSAP. Spleen cells were isolated from animals 15 days (FIGS. 3A and 3B) or 30 days (FIGS. 3C and 3D) after intratracheal conidia challenge. Animals were treated in vivo with hSAP (8 mg/kg, q2d, intranasal; filled bars) or PBS control (q2d, intranasal; open bars) for the last two weeks of the model.
Figure 3B:
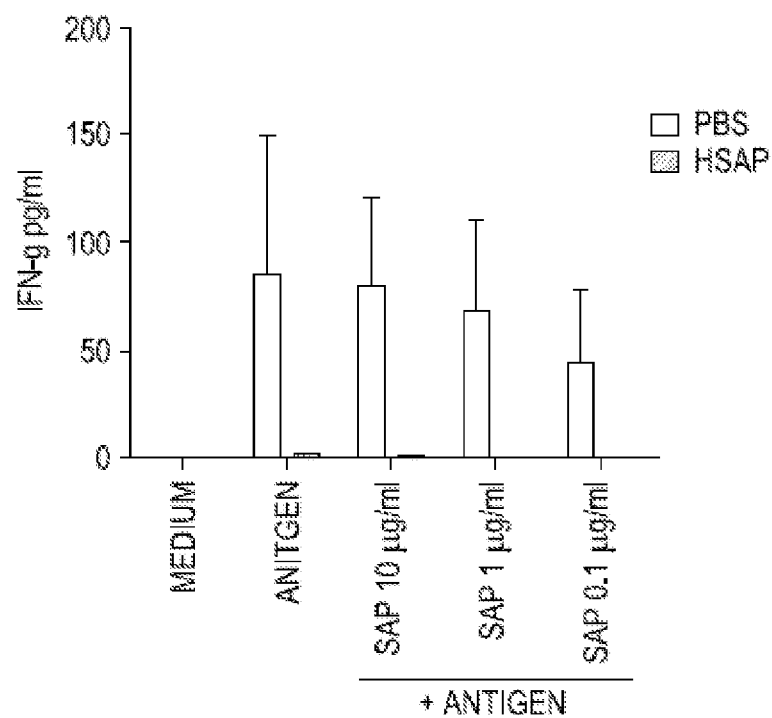
Figure 3C:
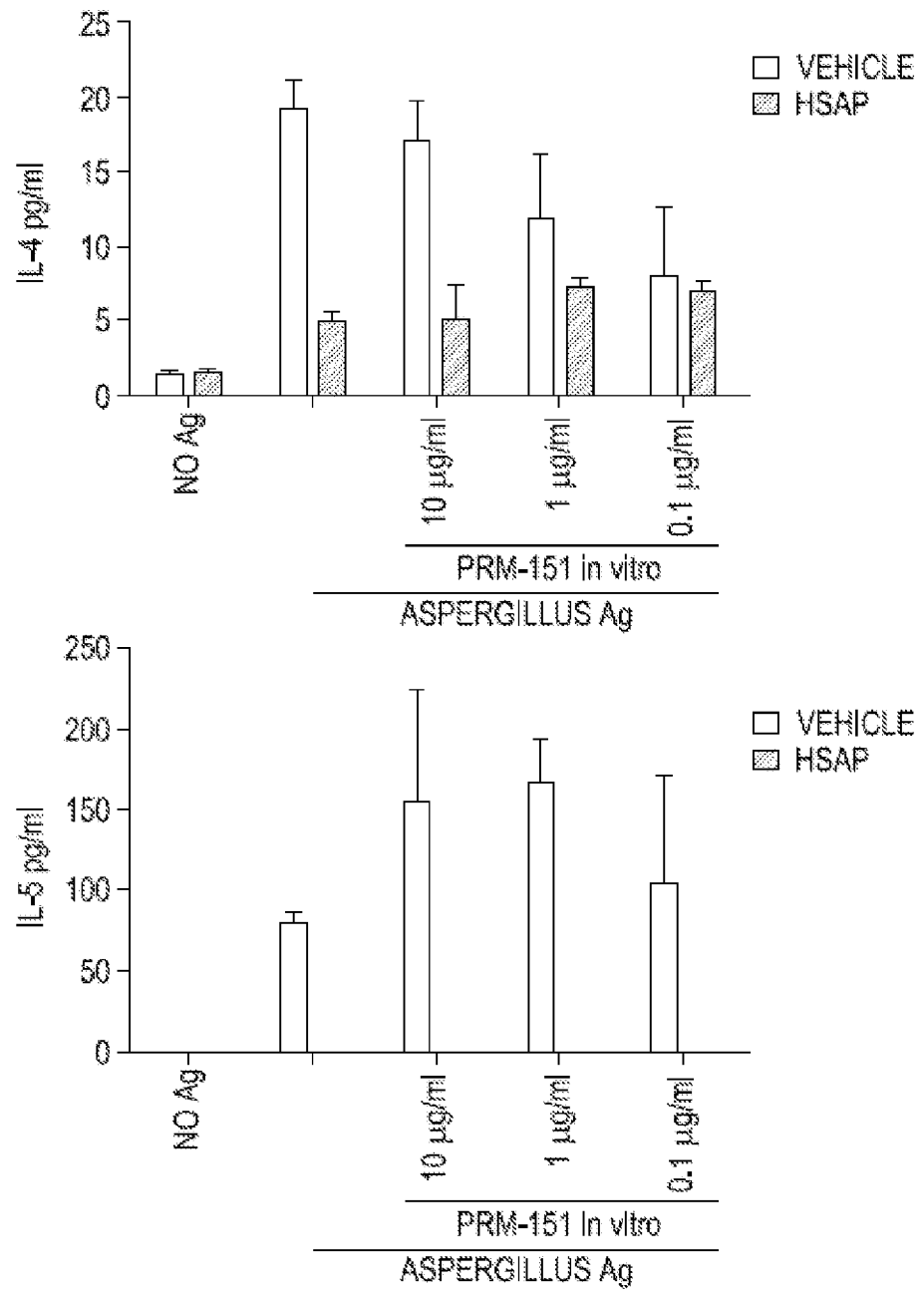
Figure 3D:
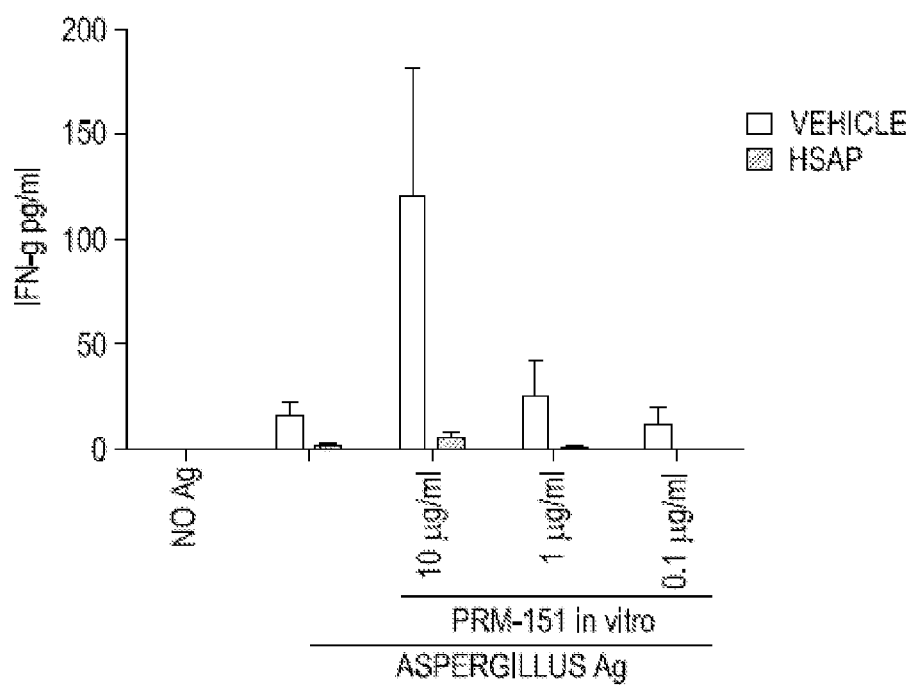

At day 15- and 30-time points (FIGS. 2A and 2B respectively), groups of five mice treated with SAP or control (PBS) were analyzed for changes in airway hyperresponsiveness (AHR). Bronchial hyperresponsiveness was assessed after an intratracheal *A. fumigatus* conidia challenge using a Buxco™ plethysmograph (Buxco, Troy, N.Y.). Briefly, sodium pentobarbital (Butler Co., Columbus, Ohio; 0.04 mg/g of mouse body weight) was used to anesthetize mice prior to their intubation and ventilation was carried out with a Harvard pump ventilator (Harvard Apparatus, Reno Nev.). Once baseline airway resistance was established, 420 mg/kg of methacholine was introduced into each mouse via cannulated tail vein, and airway hyperresponsiveness was monitored for approximately 3 minutes. The peak increase in airway resistance was then recorded. At day 15- and 30-time points (FIGS. 2A and 2B respectively), groups of five mice treated with SAP or control (PBS) were anesthetized with sodium pentobarbital and analyzed for changes in airway hyperresponsiveness. SAP significantly reduced the amount of AHR in response to intravenous methacholine challenge.

Example 2

C57BL/6 mice were similarly sensitized to a commercially available preparation of soluble *A. fumigatus* antigens as above described. Animals were treated in vivo with hSAP or PBS control for the last two weeks of the model. At day 15- and 30-time points (FIGS. 3A and 3B, and 3C and 3D, respectively), groups of five mice treated were analyzed for changes in cytokine production. Spleen cells were isolated from animals at 15 or 30 days after intratracheal conidia challenge, stimulated with *aspergillus* antigen, and treated in vitro with hSAP. Splenocyte cultures were quantified (pg/mL) for production of IL-4, IL-5, and IL-10.

Example 3

Figure 4:
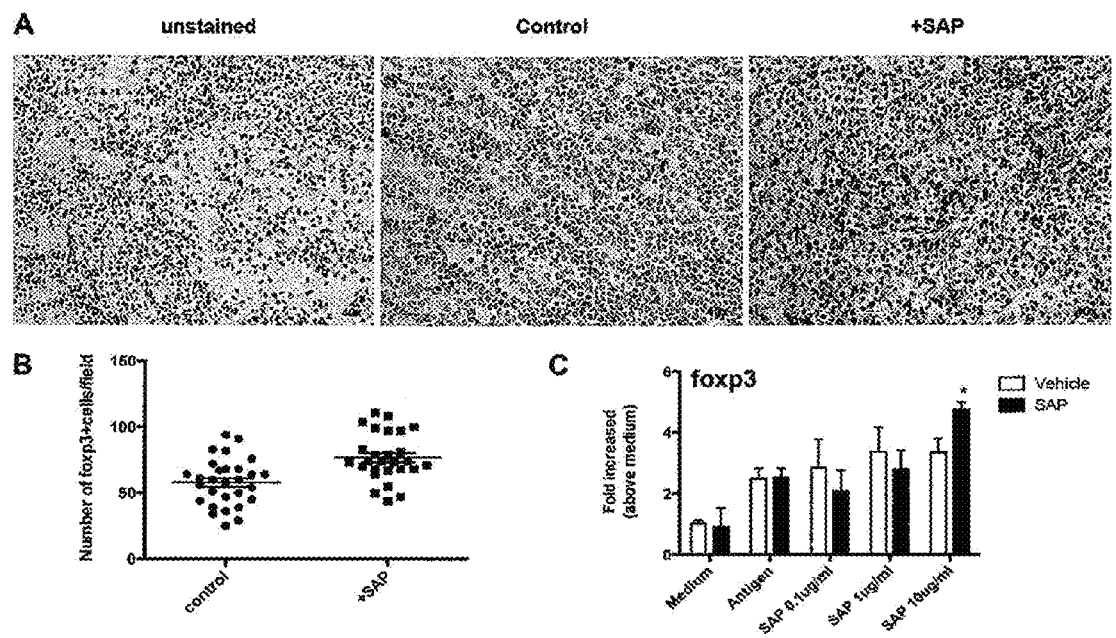
FIG. 4. FoxP3 Expression in pulmonary draining lymph nodes (A and B) or splenocyte cultures (C). A and B are from draining lymph nodes from the lung taken at day 15 from animals treated with PBS (control), or animals treated with SAP (+SAP) and stained for FoxP3. C is from splenocyte cultures that were stimulated with *Aspergillus* antigen in vitro in the presence or absence of SAP in vitro (0.1-10 μg/ml) for 24 hours. Total FoxP3 expression was quantitated using real time RT-PCR.

C57BL/6 mice were similarly sensitized to a commercially available preparation of soluble *A. fumigatus* antigens as above described. At day 15, the amount of FoxP3 expression was determined in pulmonary draining lymph nodes or splenocyte cultures. Pulmonary lymph nodes were dissected from each mouse and snap frozen in liquid $N_2$ or fixed in 10% formalin for histological analysis. Histological samples from animals treated with PBS (control) or SAP were stained for FoxP3 (FIG. 4A), and the number of FoxP3+ cells were quantified relative to each field examined (FIG. 4B). Purified splenocyte cultures were stimulated with *Aspergillus* antigen in vitro in the presence or absence of SAP in vitro (0.1-10 m/ml) for 24 hours. Total FoxP3 expression was quantitated using real time RT-PCR (FIG. 4C).

Example 4

Figure 5:
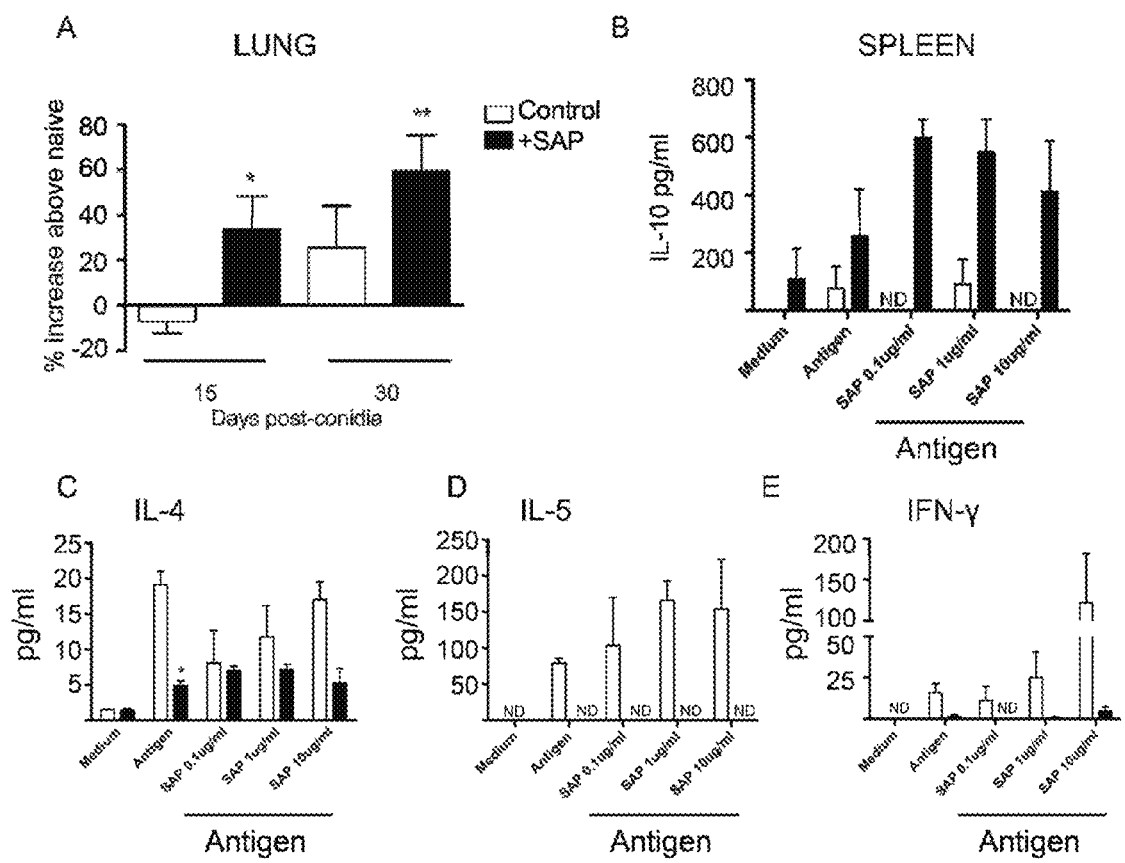
FIG. 5. Effects of SAP in vivo and in vitro on IL-10 and antigen recall. Mice were sensitized and challenged with *Aspergillus fumigatus* in vivo and treated with control (PBS, i.p., 2qd, open bars) or SAP (5 mg/kg, i.p. q2d, filled bars) on days 15-30 post-live conidia challenge. At day 30 mice were killed, A. total lung IL-10 was measured by luminex, B-E. Splenocyte cultures were stimulated in vitro with *Aspergillus fumigatus* antigen, in the presence or absence of SAP and cell-free supernatants assessed for B. IL-10, C. IL-4, D. IL-5 and E. IFN-γ protein levels by specific ELISA. Animals treated with SAP (i.p., 2qd on days 15-30) had enhanced levels of IL10 in the lungs in comparison to animals treated with PBS (i.p., q2d, on days 15-30) and compared to native, non-allergic lung. Further there was a diminished antigen recall response, indicating enhanced T regulatory cell number and/or function.

The effects of SAP in vivo and in vitro on IL-10 and antigen recall were examined. Mice were sensitized and challenged with *Aspergillus fumigatus* in vivo and treated with control (PBS, open bars) or SAP (5 mg/kg, q2d, filled bars) on days 15-30 post-live conidia challenge. At day 30, mice were sacrificed. A) Total lung IL-10 was measured by luminex. B-E) Splenocyte cultures were stimulated in vitro with *Aspergillus fumigatus* antigen, in the presence or absence of SAP (FIG. 5). Cell-free supernatants were assessed for B) IL-10, C) IL-4, D) IL-5 and E) IFN-γ protein levels by ELISA. SAP treated animals (i.p., q2d on days 15-30) had enhanced levels of IL-10 in lungs in comparison to asthma control (PBS, i.p., 2qd, on days 15-30) and levels were comparable to that in naive, non-allergic lung (FIG. 5). Splenocytes from SAP treated mice have a reduced Th1 or Th2 antigen recall response and increased IL-10. As there is also an increase in FoxP3 expression, this data indicates that SAP induces regulatory T cells within the setting of allergic airways disease.

Incorporation by Reference

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the below listed claims. The full scope of the invention should be determined by reference to the claims, along with their full scope of equivalents, and the specification, along with such variations.

I claim:

1. A method for treating an allergic airway disease in a patient, comprising administering to a patient in need thereof a therapeutically effective amount of an serum amyloid P (SAP) protein, wherein the SAP protein comprises a polypeptide comprising the amino acid sequence set forth in SEQ ID NO:1, and wherein the allergic airway disease is allergic rhinitis, allergic sinusitis, allergic-asthma, allergic bronchoconstriction, allergic dyspnea, allergic increase in mucus production in lungs, or pneumonitis.

2. The method of claim 1, wherein administration of the SAP protein reduces the number of days the patient is afflicted with the allergic airway disease.

3. The method of claim 1, wherein the SAP protein is administered topically, by injection, by intravenous injection, by inhalation, continuous release by depot or pump, or a combination thereof.

4. The method of claim 1, further comprising administering a therapeutically effective amount of an additional active agent.

5. The method of claim 4, wherein the additional active agent is selected from the group consisting of anti-IgE antibodies, short and long-term beta-agonists, corticosteroids, cromolyn, and xanthines.

6. The method of claim 1, wherein the allergic airway disease is allergic-asthma.

* * * * *

SEQUENCE LISTING

```
<160> NUMBER OF SEQ ID NOS: 4

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60
```

```
Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                 85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
            115                 120                 125

Pro Lys Ile Val Leu Gly Gln Glu Gln Asp Ser Tyr Gly Gly Lys Phe
130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
            195                 200

<210> SEQ ID NO 2
<211> LENGTH: 208
<212> TYPE: PRT
<213> ORGANISM: Gallus gallus

<400> SEQUENCE: 2

Gln Glu Asp Leu Tyr Arg Lys Val Phe Val Phe Arg Glu Asp Pro Ser
  1               5                  10                  15

Asp Ala Tyr Val Leu Leu Gln Val Gln Leu Glu Arg Pro Leu Leu Asn
                 20                  25                  30

Phe Thr Val Cys Leu Arg Ser Tyr Thr Asp Leu Thr Arg Pro His Ser
             35                  40                  45

Leu Phe Ser Tyr Ala Thr Lys Ala Gln Asp Asn Glu Ile Leu Leu Phe
         50                  55                  60

Lys Pro Lys Pro Gly Glu Tyr Arg Phe Tyr Val Gly Gly Lys Tyr Val
 65                  70                  75                  80

Thr Phe Arg Val Pro Glu Asn Arg Gly Glu Trp Glu His Val Cys Ala
                 85                  90                  95

Ser Trp Glu Ser Gly Ser Gly Ile Ala Glu Phe Trp Leu Asn Gly Arg
            100                 105                 110

Pro Trp Pro Arg Lys Gly Leu Gln Lys Gly Tyr Glu Val Gly Asn Glu
            115                 120                 125

Ala Val Val Met Leu Gly Gln Glu Gln Asp Ala Tyr Gly Gly Gly Phe
130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
                165                 170                 175

Arg Leu Pro Pro Ala Pro Leu Ala Trp Gly Arg Leu Arg Tyr Glu Ala
            180                 185                 190

Lys Gly Asp Val Val Lys Pro Arg Leu Arg Glu Ala Leu Gly Ala
            195                 200                 205

<210> SEQ ID NO 3
<211> LENGTH: 205
<212> TYPE: PRT
```

<213> ORGANISM: Bos Taurus

<400> SEQUENCE: 3

```
Gln Thr Asp Leu Arg Gly Lys Val Phe Val Phe Pro Arg Glu Ser Ser
1               5                   10                  15

Thr Asp His Val Thr Leu Ile Thr Lys Leu Glu Lys Pro Leu Lys Asn
            20                  25                  30

Leu Thr Leu Cys Leu Arg Ala Tyr Ser Asp Leu Ser Arg Gly Tyr Ser
        35                  40                  45

Leu Phe Ser Tyr Asn Ile His Ser Lys Asp Asn Glu Leu Leu Val Phe
    50                  55                  60

Lys Asn Gly Ile Gly Glu Tyr Ser Leu Tyr Ile Gly Thr Lys Val
65                  70                  75                  80

Thr Val Arg Ala Thr Glu Lys Phe Pro Ser Pro Val His Ile Cys Thr
                85                  90                  95

Ser Trp Glu Ser Ser Thr Gly Ile Ala Glu Phe Trp Ile Asn Gly Lys
            100                 105                 110

Pro Leu Val Lys Arg Gly Leu Lys Gln Gly Tyr Ala Val Gly Ala His
        115                 120                 125

Pro Lys Ile Val Leu Gly Gln Glu Gln Asp Ser Tyr Gly Gly Gly Phe
    130                 135                 140

Asp Lys Asn Gln Ser Phe Met Gly Glu Ile Gly Asp Leu Tyr Met Trp
145                 150                 155                 160

Asp Ser Val Leu Ser Pro Glu Glu Ile Leu Leu Val Tyr Gln Gly Ser
                165                 170                 175

Ser Ser Ile Ser Pro Thr Ile Leu Asp Trp Gln Ala Leu Lys Tyr Glu
            180                 185                 190

Ile Lys Gly Tyr Val Ile Val Lys Pro Met Val Trp Gly
        195                 200                 205
```

<210> SEQ ID NO 4
<211> LENGTH: 204
<212> TYPE: PRT
<213> ORGANISM: Cricetulus migratorius

<400> SEQUENCE: 4

```
Gln Thr Asp Leu Thr Gly Lys Val Phe Val Phe Pro Arg Glu Ser Glu
1               5                   10                  15

Ser Asp Tyr Val Lys Leu Ile Pro Arg Leu Glu Lys Pro Leu Glu Asn
            20                  25                  30

Phe Thr Leu Cys Phe Arg Thr Tyr Thr Asp Leu Ser Arg Pro His Ser
        35                  40                  45

Leu Phe Ser Tyr Asn Thr Lys Asn Lys Asp Asn Glu Leu Leu Ile Tyr
    50                  55                  60

Lys Glu Arg Met Gly Glu Tyr Gly Leu Tyr Ile Glu Asn Val Gly Ala
65                  70                  75                  80

Ile Val Arg Gly Val Glu Glu Phe Ala Ser Pro Val His Phe Cys Thr
                85                  90                  95

Ser Trp Glu Ser Ser Gly Ile Ala Asp Phe Trp Val Asn Gly Ile
            100                 105                 110

Pro Trp Val Lys Lys Gly Leu Lys Gly Tyr Thr Val Lys Thr Gln
        115                 120                 125

Pro Ser Ile Ile Leu Gly Gln Glu Gln Asp Asn Tyr Gly Gly Gly Phe
    130                 135                 140

Asp Lys Ser Gln Ser Phe Val Gly Glu Met Gly Asp Leu Asn Met Trp
```

-continued

```
        145                 150                 155                 160
Asp Ser Val Leu Thr Pro Glu Glu Ile Lys Ser Val Tyr Glu Gly Ser
                165                 170                 175

Trp Leu Glu Pro Asn Ile Leu Asp Trp Arg Ala Leu Asn Tyr Glu Met
                180                 185                 190

Ser Gly Tyr Ala Val Ile Arg Pro Arg Val Trp His
        195                 200
```